US012233390B2

(12) United States Patent
Cervantes et al.

(10) Patent No.: US 12,233,390 B2
(45) Date of Patent: Feb. 25, 2025

(54) NONFOULING COMPOSITIONS AND METHODS FOR MANIPULATING AND PROCESSING ENCAPSULATED DROPLETS

(71) Applicant: MIROCULUS INC., San Francisco, CA (US)

(72) Inventors: Eduardo Cervantes, San Francisco, CA (US); Mais Jehan Jebrail, Toronto (CA)

(73) Assignee: mirOculus Inc., San Francisco, CA (US)

( * ) Notice: Subject to any disclaimer, the term of this patent is extended or adjusted under 35 U.S.C. 154(b) by 803 days.

(21) Appl. No.: 17/427,290

(22) PCT Filed: Jan. 31, 2020

(86) PCT No.: PCT/US2020/016292
§ 371 (c)(1),
(2) Date: Jul. 30, 2021

(87) PCT Pub. No.: WO2020/160520
PCT Pub. Date: Aug. 6, 2020

(65) Prior Publication Data
US 2022/0161216 A1      May 26, 2022

Related U.S. Application Data

(60) Provisional application No. 62/799,734, filed on Jan. 31, 2019.

(51) Int. Cl.
*B01J 13/04*        (2006.01)
*C12N 5/00*         (2006.01)

(52) U.S. Cl.
CPC ............ *B01J 13/04* (2013.01); *C12N 5/0012* (2013.01)

(58) Field of Classification Search
CPC ... B01L 3/502792; B01J 13/04; C12N 5/0012
See application file for complete search history.

(56) References Cited

U.S. PATENT DOCUMENTS

| 4,469,863 A | 9/1984 | Ts'o et al. |
| 4,492,322 A | 1/1985 | Hieftje et al. |

(Continued)

FOREIGN PATENT DOCUMENTS

| CA | 2470847 A1 | 7/2003 |
| CA | 2740113 A1 | 4/2010 |

(Continued)

OTHER PUBLICATIONS

Chemical Book, Paraffin wax, May 16, 2024, url: https://www.chemicalbook.com/ChemicalProductProperty_EN_CB2854418.htm (Year: 2024).*

(Continued)

*Primary Examiner* — Emmanuel S Luk
*Assistant Examiner* — Elisa H Vera
(74) *Attorney, Agent, or Firm* — Shay Glenn LLP

(57) ABSTRACT

Compositions for preventing or limiting surface fouling as well as evaporation and methods for their use in air-matrix digital microfluidics (DMF) apparatuses are described. A mobilizing wax material may be used to selectively encapsulate a reaction droplet in the air gap of the apparatus, which permits the at least partially encapsulated reaction droplet to be portable within the DMF apparatus. Additional aqueous droplets may be combined with the encapsulated droplet, by merging with an aqueous droplet having a coating of a secondary material (e.g., an oil or other hydrophobic material) that may allow combining of the droplets. The compositions may be additionally useful in non-DMF applications such as laboratory protocols for hybridization, ligation and amplification.

13 Claims, 7 Drawing Sheets

(56) References Cited

U.S. PATENT DOCUMENTS

| | | |
|---|---|---|
| 4,569,575 A | 2/1986 | Le Pesant et al. |
| 4,636,785 A | 1/1987 | Le Pesant |
| 4,818,052 A | 4/1989 | Le Pesant et al. |
| 5,034,506 A | 7/1991 | Summerton et al. |
| 5,130,238 A | 7/1992 | Malek et al. |
| 5,216,141 A | 6/1993 | Benner |
| 5,235,033 A | 8/1993 | Summerton et al. |
| 5,270,185 A | 12/1993 | Margolskee |
| 5,386,023 A | 1/1995 | Sanghvi et al. |
| 5,399,491 A | 3/1995 | Kacian et al. |
| 5,409,818 A | 4/1995 | Davey et al. |
| 5,411,876 A | 5/1995 | Bloch et al. |
| 5,455,166 A | 10/1995 | Walker |
| 5,486,337 A | 1/1996 | Ohkawa |
| 5,602,240 A | 2/1997 | De Mesmaeker et al. |
| 5,637,684 A | 6/1997 | Cook et al. |
| 5,644,048 A | 7/1997 | Yau |
| 5,681,702 A | 10/1997 | Collins et al. |
| 5,705,365 A | 1/1998 | Ryder et al. |
| 5,710,029 A | 1/1998 | Ryder et al. |
| 5,806,515 A | 9/1998 | Bare et al. |
| 5,888,779 A | 3/1999 | Kacian et al. |
| 6,007,690 A | 12/1999 | Nelson et al. |
| 6,074,725 A | 6/2000 | Kennedy |
| 6,294,063 B1 | 9/2001 | Becker et al. |
| 6,352,838 B1 | 3/2002 | Krulevitch et al. |
| 6,353,149 B1 | 5/2002 | Stone |
| 6,401,552 B1 | 6/2002 | Elkins |
| 6,495,369 B1 | 12/2002 | Kercso et al. |
| 6,565,727 B1 | 5/2003 | Shenderov |
| 6,596,988 B2 | 7/2003 | Corso et al. |
| 6,656,428 B1 | 12/2003 | Clark et al. |
| 6,723,985 B2 | 4/2004 | Schultz et al. |
| 6,773,566 B2 | 8/2004 | Shenderov |
| 6,787,111 B2 | 9/2004 | Roach et al. |
| 6,887,384 B1 | 5/2005 | Frechet et al. |
| 6,911,132 B2 | 6/2005 | Pamula et al. |
| 6,989,234 B2 | 1/2006 | Kolar et al. |
| 7,057,031 B2 | 6/2006 | Olejnik et al. |
| 7,147,763 B2 | 12/2006 | Elrod et al. |
| 7,163,612 B2 | 1/2007 | Sterling et al. |
| 7,214,302 B1 | 5/2007 | Reihs et al. |
| 7,323,345 B1 | 1/2008 | Stjernstrom |
| 7,328,979 B2 | 2/2008 | Decre et al. |
| 7,329,545 B2 | 2/2008 | Pamula et al. |
| 7,349,014 B2 | 3/2008 | Higashihara |
| 7,390,463 B2 | 6/2008 | He et al. |
| 7,391,020 B2 | 6/2008 | Bousse et al. |
| 7,439,014 B1 | 10/2008 | Pamula et al. |
| 7,445,926 B2 | 11/2008 | Mathies et al. |
| 7,531,120 B2 | 5/2009 | Van Rijn et al. |
| D599,832 S | 9/2009 | Chapin et al. |
| 7,713,456 B2 | 5/2010 | Dodd et al. |
| 7,727,723 B2 | 6/2010 | Pollack et al. |
| 7,745,207 B2 | 6/2010 | Jovanovich et al. |
| 7,763,471 B2 | 7/2010 | Pamula et al. |
| 7,815,871 B2 | 10/2010 | Pamula et al. |
| 7,816,121 B2 | 10/2010 | Pollack et al. |
| 7,822,510 B2 | 10/2010 | Paik et al. |
| 7,851,184 B2 | 12/2010 | Pollack et al. |
| 7,897,737 B2 | 3/2011 | Wu et al. |
| 7,901,947 B2 | 3/2011 | Pollack et al. |
| 7,919,330 B2 | 4/2011 | de Guzman et al. |
| 7,939,021 B2 | 5/2011 | Smith et al. |
| 7,998,436 B2 | 8/2011 | Pollack et al. |
| 8,007,739 B2 | 8/2011 | Pollack et al. |
| 8,041,463 B2 | 10/2011 | Pollack et al. |
| 8,053,239 B2 | 11/2011 | Wheeler et al. |
| 8,088,578 B2 | 1/2012 | Hua et al. |
| 8,093,062 B2 | 1/2012 | Winger |
| 8,137,917 B2 | 3/2012 | Pollack et al. |
| 8,187,864 B2 | 5/2012 | Wheeler et al. |
| 8,190,371 B2 | 5/2012 | Allawi et al. |
| 8,202,686 B2 | 6/2012 | Pamula et al. |
| 8,202,736 B2 | 6/2012 | Mousa et al. |
| 8,208,146 B2 | 6/2012 | Srinivasan et al. |
| 8,268,246 B2 | 9/2012 | Srinivasan et al. |
| 8,304,253 B2 | 11/2012 | Yi et al. |
| 8,317,990 B2 | 11/2012 | Pamula et al. |
| 8,349,276 B2 | 1/2013 | Pamula et al. |
| 8,364,315 B2 | 1/2013 | Sturmer et al. |
| 8,367,370 B2 | 2/2013 | Wheeler et al. |
| 8,389,297 B2 | 3/2013 | Pamula et al. |
| 8,394,641 B2 | 3/2013 | Winger |
| 8,399,222 B2 | 3/2013 | Siva et al. |
| 8,426,213 B2 | 4/2013 | Eckhardt et al. |
| 8,440,392 B2 | 5/2013 | Pamula et al. |
| 8,454,905 B2 | 6/2013 | Pope et al. |
| 8,460,528 B2 | 6/2013 | Pollack et al. |
| 8,470,153 B2 | 6/2013 | Feiglin et al. |
| 8,470,606 B2 | 6/2013 | Srinivasan et al. |
| 8,481,125 B2 | 7/2013 | Yi et al. |
| 8,492,168 B2 | 7/2013 | Srinivasan et al. |
| 8,562,807 B2 | 10/2013 | Srinivasan et al. |
| 8,591,830 B2 | 11/2013 | Sudarsan et al. |
| 8,592,217 B2 | 11/2013 | Eckhardt |
| 8,613,889 B2 | 12/2013 | Pollack et al. |
| 8,637,317 B2 | 1/2014 | Pamula et al. |
| 8,637,324 B2 | 1/2014 | Pollack et al. |
| 8,653,832 B2 | 2/2014 | Hadwen et al. |
| 8,658,111 B2 | 2/2014 | Srinivasan et al. |
| 8,685,344 B2 | 4/2014 | Sudarsan et al. |
| 8,685,754 B2 | 4/2014 | Pollack et al. |
| 8,702,938 B2 | 4/2014 | Srinivasan et al. |
| 8,716,015 B2 | 5/2014 | Pollack et al. |
| 8,809,068 B2 | 8/2014 | Sista et al. |
| 8,821,705 B2 | 9/2014 | Bjornson et al. |
| 8,845,872 B2 | 9/2014 | Pollack et al. |
| 8,846,414 B2 | 9/2014 | Sista et al. |
| 8,852,952 B2 | 10/2014 | Pollack et al. |
| 8,872,527 B2 | 10/2014 | Sturmer et al. |
| 8,877,512 B2 | 11/2014 | Srinivasan et al. |
| 8,888,969 B2 | 11/2014 | Soleymani et al. |
| 8,901,043 B2 | 12/2014 | Eckhardt et al. |
| 8,926,065 B2 | 1/2015 | Winger |
| 8,927,296 B2 | 1/2015 | Sista et al. |
| 8,936,708 B2 | 1/2015 | Feiglin et al. |
| 8,951,732 B2 | 2/2015 | Pollack et al. |
| 8,980,198 B2 | 3/2015 | Srinivasan et al. |
| 9,005,544 B2 | 4/2015 | Van Dam et al. |
| 9,011,662 B2 | 4/2015 | Wang et al. |
| 9,039,973 B2 | 5/2015 | Watson et al. |
| 9,046,514 B2 | 6/2015 | Sista et al. |
| 9,091,649 B2 | 7/2015 | Pollack et al. |
| 9,140,635 B2 | 9/2015 | Graham et al. |
| 9,188,615 B2 | 11/2015 | Sturmer et al. |
| 9,223,317 B2 | 12/2015 | Winger |
| 9,238,222 B2 | 1/2016 | Delattre et al. |
| 9,248,450 B2 | 2/2016 | Bauer |
| 9,377,439 B2 | 6/2016 | Lee et al. |
| 9,435,765 B2 | 9/2016 | Reimitz et al. |
| 9,446,404 B2 | 9/2016 | Bauer et al. |
| 9,476,811 B2 | 10/2016 | Mudrik et al. |
| 9,476,856 B2 | 10/2016 | Pamula et al. |
| 9,513,253 B2 | 12/2016 | Winger |
| 9,517,469 B2 | 12/2016 | Shenderov et al. |
| 9,594,056 B2 | 3/2017 | Fobel et al. |
| 9,851,365 B2 | 12/2017 | Mousa et al. |
| 9,975,117 B2 | 5/2018 | Lee et al. |
| 10,232,374 B2 | 3/2019 | Jebrail et al. |
| 10,464,067 B2 | 11/2019 | Jebrail et al. |
| 10,596,572 B2 | 3/2020 | Hong et al. |
| 10,695,762 B2 | 6/2020 | Jebrail et al. |
| 11,097,276 B2 | 8/2021 | Jebrail et al. |
| 2002/0150683 A1 | 10/2002 | Trojan et al. |
| 2003/0017551 A1 | 1/2003 | Parthasarathy et al. |
| 2003/0136451 A1 | 7/2003 | Beebe et al. |
| 2003/0194716 A1 | 10/2003 | Knoll |
| 2004/0171169 A1 | 9/2004 | Kallury et al. |
| 2004/0211659 A1 | 10/2004 | Velev |
| 2005/0115836 A1 | 6/2005 | Reihs |
| 2005/0133370 A1 | 6/2005 | Park et al. |
| 2005/0148091 A1 | 7/2005 | Kitaguchi et al. |
| 2005/0191759 A1 | 9/2005 | Bjergaard et al. |

(56) References Cited

U.S. PATENT DOCUMENTS

| | | |
|---|---|---|
| 2005/0220675 A1 | 10/2005 | Reed et al. |
| 2006/0091015 A1 | 5/2006 | Lau |
| 2006/0132542 A1 | 6/2006 | Bruker et al. |
| 2006/0231398 A1 | 10/2006 | Sarrut et al. |
| 2006/0272942 A1 | 12/2006 | Sirringhaus |
| 2007/0023292 A1 | 2/2007 | Kim et al. |
| 2007/0095407 A1 | 5/2007 | Chen et al. |
| 2007/0138664 A1 | 6/2007 | Chen et al. |
| 2007/0148763 A1 | 6/2007 | Huh et al. |
| 2007/0258864 A1 | 11/2007 | Braymer et al. |
| 2007/0269825 A1 | 11/2007 | Wang et al. |
| 2008/0110753 A1 | 5/2008 | Fourrier et al. |
| 2008/0131904 A1 | 6/2008 | Parce et al. |
| 2008/0156983 A1 | 7/2008 | Fourrier et al. |
| 2008/0169197 A1 | 7/2008 | McRuer et al. |
| 2008/0185339 A1 | 8/2008 | Delapierre et al. |
| 2008/0210558 A1 | 9/2008 | Sauter-Starace et al. |
| 2008/0211849 A1 | 9/2008 | Pierik et al. |
| 2008/0241831 A1 | 10/2008 | Fan et al. |
| 2008/0293051 A1 | 11/2008 | Levy et al. |
| 2009/0017197 A1 | 1/2009 | Zhang et al. |
| 2009/0017453 A1 | 1/2009 | Maples et al. |
| 2009/0051736 A1 | 2/2009 | Sugahara |
| 2009/0124721 A1 | 5/2009 | Chen et al. |
| 2009/0207206 A1 | 8/2009 | Harada |
| 2009/0286297 A1 | 11/2009 | Pihl et al. |
| 2010/0015614 A1 | 1/2010 | Beer et al. |
| 2010/0022414 A1 | 1/2010 | Link et al. |
| 2010/0025250 A1 | 2/2010 | Pamula et al. |
| 2010/0032293 A1 | 2/2010 | Pollack et al. |
| 2010/0048410 A1 | 2/2010 | Shenderov et al. |
| 2010/0087012 A1 | 4/2010 | Shenderov |
| 2010/0120130 A1 | 5/2010 | Srinivasan et al. |
| 2010/0130369 A1 | 5/2010 | Shenderov et al. |
| 2010/0136544 A1 | 6/2010 | Agresti et al. |
| 2010/0206094 A1 | 8/2010 | Shenderov |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0270156 A1 | 10/2010 | Srinivasan et al. |
| 2010/0288368 A1 | 11/2010 | Beebe et al. |
| 2010/0311599 A1 | 12/2010 | Wheeler et al. |
| 2011/0024793 A1 | 2/2011 | Jeon |
| 2011/0076685 A1 | 3/2011 | Moeller et al. |
| 2011/0097763 A1 | 4/2011 | Pollack et al. |
| 2011/0104725 A1 | 5/2011 | Pamula et al. |
| 2011/0104747 A1 | 5/2011 | Pollack et al. |
| 2011/0107822 A1 | 5/2011 | Bunner et al. |
| 2011/0147216 A1 | 6/2011 | Fan et al. |
| 2011/0220501 A1 | 9/2011 | Witkowski et al. |
| 2011/0240471 A1 | 10/2011 | Wheeler et al. |
| 2011/0247934 A1 | 10/2011 | Wang et al. |
| 2011/0293851 A1 | 12/2011 | Bollström et al. |
| 2011/0303542 A1 | 12/2011 | Srinivasan et al. |
| 2011/0311980 A1 | 12/2011 | Pollack et al. |
| 2012/0000777 A1 | 1/2012 | Garrell et al. |
| 2012/0045748 A1 | 2/2012 | Willson et al. |
| 2012/0045768 A1 | 2/2012 | Arunachalam et al. |
| 2012/0149018 A1 | 6/2012 | Dahlberg et al. |
| 2012/0190027 A1 | 7/2012 | Loeffert et al. |
| 2012/0208705 A1 | 8/2012 | Steemers et al. |
| 2012/0208724 A1 | 8/2012 | Steemers et al. |
| 2012/0259233 A1 | 10/2012 | Chan et al. |
| 2012/0261264 A1 | 10/2012 | Srinivasan et al. |
| 2012/0289581 A1 | 11/2012 | Chang et al. |
| 2012/0325665 A1 | 12/2012 | Chiou et al. |
| 2013/0017544 A1 | 1/2013 | Eckhardt et al. |
| 2013/0018611 A1 | 1/2013 | Sturmer |
| 2013/0062205 A1 | 3/2013 | Hadwen et al. |
| 2013/0068622 A1 | 3/2013 | Schertzer et al. |
| 2013/0105318 A1 | 5/2013 | Bhattacharya et al. |
| 2013/0123979 A1 | 5/2013 | Elliot et al. |
| 2013/0157259 A1 | 6/2013 | Choi et al. |
| 2013/0168250 A1 | 7/2013 | Fogleman et al. |
| 2013/0171546 A1 | 7/2013 | White et al. |
| 2013/0177915 A1 | 7/2013 | Too et al. |
| 2013/0203606 A1 | 8/2013 | Pollack et al. |
| 2013/0215492 A1 | 8/2013 | Steckl et al. |
| 2013/0217113 A1 | 8/2013 | Srinivasan et al. |
| 2013/0225450 A1 | 8/2013 | Pollack et al. |
| 2013/0236377 A1 | 9/2013 | Kim et al. |
| 2013/0270114 A1 | 10/2013 | Feiglin |
| 2013/0284956 A1 | 10/2013 | Kwon |
| 2013/0288254 A1 | 10/2013 | Pollack et al. |
| 2013/0293246 A1 | 11/2013 | Pollack et al. |
| 2013/0306480 A1 | 11/2013 | Chang et al. |
| 2014/0005066 A1 | 1/2014 | Boles et al. |
| 2014/0054174 A1 | 2/2014 | Wang |
| 2014/0124037 A1 | 5/2014 | Foley |
| 2014/0141409 A1 | 5/2014 | Foley et al. |
| 2014/0161686 A1 | 6/2014 | Bort et al. |
| 2014/0174926 A1 | 6/2014 | Bort et al. |
| 2014/0179539 A1 | 6/2014 | Lohman et al. |
| 2014/0194305 A1 | 7/2014 | Kayyem et al. |
| 2014/0216559 A1 | 8/2014 | Foley |
| 2014/0272965 A1 | 9/2014 | Handique et al. |
| 2014/0273100 A1 | 9/2014 | Saito et al. |
| 2014/0335069 A1 | 11/2014 | Graham et al. |
| 2014/0353157 A1 | 12/2014 | Hoffmeyer et al. |
| 2015/0001078 A1 | 1/2015 | Feiglin |
| 2015/0008123 A1 | 1/2015 | Cheng et al. |
| 2015/0021182 A1 | 1/2015 | Rival et al. |
| 2015/0075986 A1 | 3/2015 | Cyril et al. |
| 2015/0111237 A1 | 4/2015 | Graham et al. |
| 2015/0144489 A1 | 5/2015 | Hoffmeyer et al. |
| 2015/0148549 A1 | 5/2015 | Van dam et al. |
| 2015/0198604 A1 | 6/2015 | Ermantraut et al. |
| 2015/0205272 A1 | 7/2015 | Yi et al. |
| 2015/0212043 A1 | 7/2015 | Pollack |
| 2015/0238959 A1 | 8/2015 | Prakash et al. |
| 2015/0258520 A1 | 9/2015 | Griffiths et al. |
| 2015/0267242 A1 | 9/2015 | Foegeding et al. |
| 2015/0322272 A1 | 11/2015 | Pokroy et al. |
| 2016/0068901 A1 | 3/2016 | Eckhardt et al. |
| 2016/0108432 A1 | 4/2016 | Punnamaraju et al. |
| 2016/0108433 A1 | 4/2016 | Fair et al. |
| 2016/0116438 A1 | 4/2016 | Pamula et al. |
| 2016/0129437 A1 | 5/2016 | Kayyem et al. |
| 2016/0161343 A1 | 6/2016 | Smith et al. |
| 2016/0175859 A1 | 6/2016 | Yi et al. |
| 2016/0199832 A1 | 7/2016 | Jamshidi et al. |
| 2016/0273032 A1 | 9/2016 | Esfandyarpour |
| 2016/0298173 A1 | 10/2016 | Wang et al. |
| 2016/0319354 A1 | 11/2016 | Tocigl et al. |
| 2016/0370317 A9 | 12/2016 | Sudarsan et al. |
| 2017/0184546 A1 | 6/2017 | Fobel et al. |
| 2017/0315090 A1 | 11/2017 | Wheeler et al. |
| 2017/0354973 A1 | 12/2017 | Sustarich et al. |
| 2018/0001286 A1 | 1/2018 | Wu |
| 2018/0015469 A1 | 1/2018 | Reiter et al. |
| 2018/0059056 A1 | 3/2018 | Taylor et al. |
| 2018/0095067 A1 | 4/2018 | Huff et al. |
| 2018/0099275 A1 | 4/2018 | Wu et al. |
| 2018/0120335 A1 | 5/2018 | Mousa et al. |
| 2018/0193831 A1 | 7/2018 | Hopper |
| 2018/0221882 A1 | 8/2018 | Roberts et al. |
| 2018/0250672 A1 | 9/2018 | Jamshidi et al. |
| 2019/0060900 A1 | 2/2019 | Breinlinger et al. |
| 2019/0168223 A1 | 6/2019 | Soto-Moreno et al. |
| 2019/0210026 A1 | 7/2019 | Jebrail et al. |
| 2019/0329258 A1 | 10/2019 | Kinney et al. |
| 2019/0374950 A1* | 12/2019 | Fobel .................... C09D 5/008 |
| 2020/0061621 A1 | 2/2020 | Jebrail et al. |
| 2020/0114359 A1 | 4/2020 | Jebrail et al. |
| 2020/0164367 A1 | 5/2020 | Wunsch et al. |
| 2020/0179933 A1 | 6/2020 | Jebrail et al. |
| 2020/0254458 A1 | 8/2020 | Hong et al. |
| 2020/0261913 A1 | 8/2020 | Williams et al. |
| 2020/0316606 A1 | 10/2020 | Soto-Moreno et al. |
| 2020/0324290 A1 | 10/2020 | Jebrail et al. |
| 2021/0069714 A1 | 3/2021 | Jebrail et al. |
| 2021/0291175 A1 | 9/2021 | Gartner et al. |
| 2021/0370304 A1 | 12/2021 | Jebrail et al. |
| 2022/0118455 A1 | 4/2022 | Jebrail et al. |

(56) References Cited

U.S. PATENT DOCUMENTS

| | | |
|---|---|---|
| 2022/0401957 A1 | 12/2022 | Jebrail et al. |
| 2023/0049633 A1 | 2/2023 | Jebrail et al. |
| 2023/0219083 A1 | 7/2023 | Jebrail et al. |
| 2023/0219092 A1 | 7/2023 | Jebrail et al. |
| 2023/0249185 A1 | 8/2023 | Jebrail et al. |
| 2023/0398541 A1 | 12/2023 | Soto-moreno et al. |
| 2024/0198343 A1 | 6/2024 | Jebrail et al. |

FOREIGN PATENT DOCUMENTS

| | | |
|---|---|---|
| CA | 2881783 A1 | 2/2014 |
| CN | 1668527 A | 9/2005 |
| CN | 101609063 A | 12/2009 |
| CN | 102549804 A | 7/2012 |
| CN | 102719526 A | 10/2012 |
| CN | 102740976 A | 10/2012 |
| CN | 102836653 A | 12/2012 |
| CN | 103014148 A | 4/2013 |
| CN | 103170383 A | 6/2013 |
| CN | 103502386 A | 1/2014 |
| CN | 103946712 A | 7/2014 |
| CN | 104144748 A | 11/2014 |
| CN | 104321141 A | 1/2015 |
| CN | 104995261 A | 10/2015 |
| CN | 105764490 A | 7/2016 |
| CN | 105849032 A | 8/2016 |
| CN | 106092865 A | 11/2016 |
| DE | 19949735 A1 | 5/2001 |
| EP | 2111554 B1 | 5/2013 |
| GB | 2533952 A | 7/2016 |
| JP | 2002321449 A | 11/2002 |
| JP | 2006220606 A | 8/2006 |
| JP | 2010500596 A | 1/2010 |
| JP | 2010098133 A | 4/2010 |
| JP | 2010515877 A | 5/2010 |
| JP | 2010180222 A | 8/2010 |
| JP | 2012525687 A | 10/2012 |
| JP | 2015529615 A | 10/2015 |
| WO | WO2000/067907 A2 | 11/2000 |
| WO | WO2001/025137 A1 | 4/2001 |
| WO | WO2003/045556 A2 | 6/2003 |
| WO | WO-2004055260 A1 * | 7/2004 | ........... A61K 9/0048 |
| WO | WO2004/074169 A1 | 9/2004 |
| WO | WO2005/068993 A1 | 7/2005 |
| WO | WO2005/118129 A1 | 12/2005 |
| WO | WO2006/000828 A2 | 1/2006 |
| WO | WO2006/102309 A2 | 9/2006 |
| WO | WO2007/120240 A2 | 10/2007 |
| WO | WO2007/123908 A2 | 11/2007 |
| WO | WO2007/130294 A2 | 11/2007 |
| WO | WO2007/136386 A2 | 11/2007 |
| WO | WO2008/066828 A2 | 6/2008 |
| WO | WO2009/026339 A2 | 2/2009 |
| WO | WO2009/052348 A2 | 4/2009 |
| WO | WO2009/111723 A1 | 9/2009 |
| WO | WO2009/111769 A2 | 9/2009 |
| WO | WO2009/140671 A2 | 11/2009 |
| WO | WO2010/003188 A1 | 1/2010 |
| WO | WO2010/006166 A2 | 1/2010 |
| WO | WO2010/027894 A2 | 3/2010 |
| WO | WO2010/042637 A2 | 4/2010 |
| WO | WO2010/069977 A1 | 6/2010 |
| WO | WO2010/091334 A2 | 8/2010 |
| WO | WO2010/111265 A1 | 9/2010 |
| WO | WO2011/002957 A2 | 1/2011 |
| WO | WO2011/062557 A1 | 5/2011 |
| WO | WO2012/061832 A1 | 5/2012 |
| WO | WO2012/172172 A1 | 12/2012 |
| WO | WO2013/006312 A2 | 1/2013 |
| WO | WO2013/040562 A2 | 3/2013 |
| WO | WO2013/090889 A1 | 6/2013 |
| WO | WO2013/096839 A1 | 6/2013 |
| WO | WO2013/116039 A1 | 8/2013 |
| WO | WO2013/176767 A1 | 11/2013 |
| WO | WO2014/078100 A1 | 5/2014 |
| WO | WO2014/083622 A1 | 6/2014 |
| WO | WO2014/100473 A1 | 6/2014 |
| WO | WO2014/106167 A1 | 7/2014 |
| WO | WO2014/108185 A1 | 7/2014 |
| WO | WO2014/183118 A1 | 11/2014 |
| WO | WO2015/023745 A1 | 2/2015 |
| WO | WO2015/077737 A1 | 5/2015 |
| WO | WO2015/172255 A1 | 11/2015 |
| WO | WO2015/172256 A1 | 11/2015 |
| WO | WO2016/006184 A1 | 1/2016 |
| WO | WO2016/094589 A1 | 6/2016 |
| WO | WO2016/128544 A1 | 8/2016 |
| WO | WO2016/182814 A2 | 11/2016 |
| WO | WO2016/197013 A1 | 12/2016 |
| WO | WO-2016197103 A1 * | 12/2016 | ........ B01L 3/502792 |
| WO | WO2017/094021 A1 | 6/2017 |
| WO | WO2017/223026 A1 | 12/2017 |
| WO | WO2018/119253 A1 | 6/2018 |
| WO | WO2018/126082 A1 | 7/2018 |
| WO | WO2019/023133 A1 | 1/2019 |
| WO | WO2019/046860 A1 | 3/2019 |
| WO | WO2019/075211 A1 | 4/2019 |
| WO | WO2019/226919 A1 | 11/2019 |
| WO | WO2020/160520 A1 | 8/2020 |
| WO | WO2020/176816 A8 | 9/2020 |
| WO | WO2021/016614 A1 | 1/2021 |
| WO | WO2021/092325 A1 | 5/2021 |

OTHER PUBLICATIONS

Abdelgawad et al., All-terrain droplet actuation, Lab on a Chip, 8(5), pp. 672-677, May 2008.

Abdelgawad et al.; Low-cost, rapid-prototyping of digital microfluidics devices, Microfluidics and Nanofluidics, 4, pp. 349-355, Apr. 2008.

Abdelgawad et al.; Rapid prototyping in copper substrates for digital microfluidics, Adv. Mater., 19(1), pp. 133-137; Jan. 2007.

Abdelgawad et al; Hybrid microfluidics: a digital-to-channel interface for in-line sample processing and chemical separations, Lab on a Chip, 9(8), pp. 1046-1051, Apr. 2009.

Abdelgawad; Digital Microfluidics for Integration of Lab-on-a-Chip Devices (Doctoral dissertation); University of Toronto; © 2009.

Albrecht et al.; Laboratory testing of gonadal steroids in children; Pediatric Endocrinology Reviews; 5(suppl 1); pp. 599-607; Oct. 2007.

Analog Devices; 24-bit Capicitance-to-Digital converter with temperature sensor, AD7745/AD7746; Analog Devices; Norwood, MA; 28 pages; (year of pub. sufficiently earlier than effective US filing date and any foreign priority date) 2005.

Analog Devices; Extending the capacitive input range of AD7745/AD7746 Capicitance-to-Digital converter; Analog Devices; Norwood, MA; 5 pages; (year of pub. sufficiently earlier than effective US filing date and any foreign priority date) 2009.

Ankarberg-Lindren et al.; A purification step prior to commercial sensitive immunoassay is necessary to achieve clinical usefulness when quantifying serum 17 ?-estradiol in prepubertal children. Eur J Endocrinol, 158, pp. 117-124, Jan. 2008.

Armstrong et al.; A study of plasma free amino acid levels. II. Normal values for children and adults, Metabolism, 22(4), pp. 561-569, Apr. 1973.

Asiello et al.; Miniaturized isothermal nucleic acid amplification, a review; Lab Chip; 11(8); pp. 1420-1430; Apr. 2011.

Au et al., Integrated microbioreactor for culture and analysis of bacteria, algae and yeast, Biomedical Microdevices, 13(1), pp. 41-50, Feb. 2011.

Au et al.; A new angle on pluronic additives: Advancing droplets and understanding in digital microfluidics; Langmuir; 27; pp. 8586-8594; Jun. 2011.

Banatvala et al., Rubella, The Lancet, 363(9415), pp. 1127-1137, Apr. 2004.

Banér et al.; Signal amplification of padlock probes by rolling circle replication; Nuc. Acids Res., 26(22); pp. 5073-5078; Nov. 1998.

(56) References Cited

OTHER PUBLICATIONS

Barany; Genetic disease detection and DNA amplification using cloned thermostable ligase; PNAS; 88(1); pp. 189-193; Jan. 1991.
Barbulovic-Nad et al., A microfluidic platform for complete mammalian cell culture, Lab on a Chip, 10(12), pp. 1536-1542; Jun. 2010.
Barbulovic-Nad et al.; Digital microfluidics for cell-based assays, Lab Chip, 8(4), pp. 519-526; Apr. 2008.
Baxendale et al.; Multistep synthesis using modular flow reactors: bestmann-ohira reagent for the formation of alkynes and triazoles; Angewandle Chemie International Edition; 48(22); pp. 4017-4021; May 2009.
Beattie et al.; Endogenous sex hormones, breast cancer risk, and tamoxifen response: an ancillary study in the NSABP Breast Cancer Prevention Trial P-1, J Natl Cancer Inst, 98(2), pp. 110-115, Jan. 2006.
Beaucage et al., The Functionalization of Oligonucleotides via Phosphoramidite Derivatives, Tetrahedron, 49(10), pp. 1925-1963, Mar. 1993.
Belanger et al.; Omental and subcutaneous adipose tissue steroid levels in obese men. Steroids, 71(8), pp. 674-682, Aug. 2006.
Bergkvist et al., Improved chip design for integrated solid-phase microextraction in on-line proteomic sample preparation, Proteomics, 2(4), pp. 422-429, Apr. 2002.
Bi et al.; Dumbbell probe-mediated cascade isothermal amplification: A novel strategy for label-free detection of microRNAs and its application to real sample assay; Analytica Chimica Acta; 760; pp. 69-74; Jan. 2013.
Blankenstein et al.; Intratumoral levels of estrogens in breast cancer. J Steroid Biochem Mol Biol, 69(1-6), pp. 293-297, Apr.-Jun. 1999.
Bodamer et al.; Expanded newborn screening in Europe, Journal of Inherited Metabolic Disease, 30(4), pp. 439-444, Aug. 2007.
Bohlen et al.; Fluorometric assay of proteins in the nanogram range, Archives of Biochemistry and Biophysics, 155(1), pp. 213-220, Mar. 1973.
Boles et al.; Droplet-Based Pyrosequencing Using Digital Microfluidics; Analytical Chemistry; 83(22); pp. 8439-8447; Oct. 14, 2011.
Bollström et al.; A Multilayer Coated Fiber-Based Substrate Suitable For Printed Functionality; Organic Electronics; 10(5); pp. 1020-1023; Aug. 2009.
Bonneil et al., Integration of solid-phase extraction membranes for sample multiplexing: Application to rapid protein identification from gel-isolated protein extracts, Electrophoresis, 23(20), pp. 3589-3598, Oct. 2002.
Brassard et al.; Water-oil core-shell droplets for electrowetting-based digital microfluidic devices; Lab Chip; 8(8); pp. 1342-1349; Aug. 2008.
Brill et al., Synthesis of oligodeoxynucleoside phosphorodithioates via thioamidites, J. Am. Chem. Soc., 111(6), pp. 2321-2322, Mar. 1989.
Brivio et al.; Integrated microfluidic system enabling (bio)chemical reactions with on-line MALDI-TOF mass spectrometry, Anal. Chem., 74(16), pp. 3972-3976, Aug. 2002.
Burstein; Aromatase inhibitor-associated arthralgia syndrome. Breast, 16(3), pp. 223-234, Jun. 2007.
Carlsson et al., Screening for genetic mutations, Nature, 380(6571), pp. 207, Mar. 1996.
Chace et al.; A biochemical perspective on the use of tandem mass spectrometry for newborn screening and clinical testing, Clinical Biochemistry, 38(4), pp. 296-309; Apr. 2005.
Chace et al.; Rapid diagnosis of maple syrup urine disease in blood spots from newborns by tandem mass spectrometry, Clinical Chemistry, 41(1), pp. 62-68, Jan. 1995.
Chace et al.; Rapid diagnosis of phenylketonuria by quantitative analysis for phenylalanine and tyrosine in neonatal blood spots by tandem mass spectrometry, Clinical Chemistry, 39(1), pp. 66-71; Jan. 1993.
Chace et al.; Use of tandem mass spectrometry for multianalyte screening of dried blood specimens from newborns, Clinical Chemistry, 49(11), pp. 1797-1817, Nov. 2003.
Chace; Mass spectrometry in newborn and metabolic screening: historical perspective and future directions, Journal of Mass Spectrometry, 44(2), pp. 163-170, Feb. 2009.
Chang et al.; Integrated polymerase chain reaction chips utilizing digital microfluidics; Biomedical Microdevices; 8(3); pp. 215-225; Sep. 2006.
Chatterjee et al.; Droplet-based microfluidics with nonaqueous solvents and solutions, Lab Chip, 6(2), pp. 199-206, Feb. 2006.
Chen et al.; Selective Wettability Assisted Nanoliter Sample Generation Via Electrowetting-Based Transportation; Proceedings of the 5th International Conference on Nanochannels, Microchannels and Minichannels (ICNMM); Puebla, Mexico; Paper No. ICNMM2007-30184; pp. 147-153; Jun. 18-20, 2007.
Chen et al.; The chemistrode: a droplet-based microfluidic device for stimulation and recording with high temporal, spatial, and chemical resolution; Proceedings of the National Academy of Sciences; 105(44); pp. 16843-16848; Nov. 2004.
Cheng et al., Paper-Based ELISA, Angewandte Chemie, 49(28), pp. 4771-4774, Jun. 2010.
Cheng et al.; Highly Sensitive Determination of microRNA Using Target-Primed and Branched Rolling-Circle Amplification; Angew. Chem.; 121(18); pp. 3318-3322; Apr. 2009.
Chetrite et al.; Estradiol inhibits the estrone sulfatase activity in normal and cancerous human breast tissues. Journal of Steroid Biochemistry and Molecular Biology, 104(3-5), pp. 289-292, May 2007.
Cho et al.; Creating, transporting, cutting, and merging liquid droplets by electrowetting-based actuation for digital microfluidic circuits, J. MEMS 2003, 12(1), pp. 70-80, Feb. 2003.
Choi et al., Automated digital microfluidic platform for magnetic-particle-based immunoassays with optimization by design of experiments, Anal. Chem., 85(20), pp. 9638-9646; Oct. 2013.
Choi et al., Digital Microfluidics, Annu. Rev. Anal. Chem., 5, pp. 413-440, (Epub) Apr. 2012.
Christiansen; Hormone Replacement Therapy and Osteoporosis; Maturitas, 23, Suppl. pp. S71-S76, May 1996.
Chuang et al.; Direct Handwriting Manipulation of Droplets By Self-Aligned Mirror—EWOO Across A Dielectric Sheet; 19th IEEE International Conf. on Micro Electro Mechanical Systems (MEMS); Instanbul, Turkey; pp. 538-541; Jan. 22-26, 2006.
Cipriano et al.; The cost-effectiveness of expanding newborn screening for up to 21 inherited metabolic disorders using tandem mass spectrometry: results from a decision-analytic model, Value in Health, 10(2), pp. 83-97, Mar.-Apr. 2007.
Cooney et al.; Electrowetting droplet microfluidics on a single planar surface, Microfluid. Nanofluid., 2(5), pp. 435-446; Sep. 2006.
Coregenomics; How do SPRI beads work; 31 pages; retrieved from the internet (http://core-genomics.blogspot.com/2012/04/how-do-spri-beads-work.html); Apr. 28, 2012.
Cottam et al.; Accelerated synthesis of titanium oxide nanostructures using microfluidic chips; Lab on a Chip; 7(2); pp. 167-169; Feb. 2007.
Crabtree et al.; Microchip injection and separation anomalies due to pressure effects, Anal. Chem., 73(17), pp. 4079-4086, Sep. 2001.
Cunningham; Testosterone replacement therapy for late-onset hypogonadism. Nature Clinical Practice Urology, 3(5), pp. 260-267, May 2006.
Cuzick; Chemoprevention of breast cancer. Women's Health, 2(6), pp. 853-861, Nov. 2006.
Dahlin et al.; Poly(dimethylsiloxane)-based microchip for two-dimensional solid-phase extraction-capillary electrophoresis with an integrated electrospray emitter tip, Anal. Chem., 77(16), pp. 5356-5363, Aug. 2005.
Dambrot; Of microchemistry and molecules: Electronic microfluidic device synthesizes biocompatible probes; 4 pages, retrieved from the internet (https://phys.org/news/2012-01-microchemistry-molecules-electronic-microfluidic-device.html); Jan. 26, 2012.
Danton et al.; Porphyrin profiles in blood, urine and faeces by HPLC/electrospray ionization tandem mass spectrometry. Biomedical Chromatography, 20(6-7), pp. 612-621, Jun.-Jul. 2006.

(56) References Cited

OTHER PUBLICATIONS

De Mesmaeker et al.; Comparison of rigid and flexible backbones in antisense oligonucleotides; Bioorganic & Medicinal Chem. Lett; 4(3); pp. 395-398; Feb. 1994.

Deligeorgiev et al.; Intercalating Cyanine Dyes for Nucleic Acid Detection; Recent Pat Mat Sci; 2(1); pp. 1-26; Jan. 2006.

Dempcy et al., Synthesis of a thymidyl pentamer of deoxyribonucleic guanidine and binding studies with DNA homopolynucleotides, Proc. Natl. Acad. Sci., 92(13), pp. 6097-6101, Jun. 1995.

Deng et al.; Rapid determination of amino acids in neonatal blood samples based on derivatization with isobutyl chloroformate followed by solid-phase microextraction and gas chromatography/mass spectrometry. Rapid Communications in Mass Spectrometry, 18(1), pp. 2558-2564, Nov. 2004.

Denneulin et al.; Infra-red assisted sintering of inkjet printed silver tracks on paper substrates; J Nanopart Res; 13(9); pp. 3815-3823; Sep. 2011.

Dibbelt et al.; Determination of natural and synthetic estrogens by radioimmunoassay: Comparison of direct and extraction methods for quantification of estrone in human serum. Clinical Laboratory, 44(3), 137-143, Mar. 1998.

Dietzen et al.; National academy of clinical biochemistry laboratory medicine practice guidelines: follow-up testing for metabolic disease identified by expanded newborn screening using tandem mass spectrometry; executive summary, Clinical Chemistry, 55(9), pp. 1615-1626, Sep. 2009.

Diver et al.; Warning on plasma oestradiol measurement. Lancet, 330(8567), p. 1097, Nov. 1987.

Divino Filho et al.; Simultaneous measurements of free amino acid patterns of plasma, muscle and erythrocytes in healthy human subjects, Clinical Nutrition, 16(6), pp. 299-305, Dec. 1997.

Dixon et al.; An inkjet printed, roll-coated digital microfluidic device for inexpensive, miniaturized diagnostic assays; Lab on a Chip; 16(23); pp. 4560-4568; Nov. 2016.

Djerassi; Chemical birth of the pill. American Journal of Obstetrics and Gynecology, 194(1), pp. 290-298, Jan. 2006.

Dobrowolski et al.; DNA microarray technology for neonatal screening, Acta Paediatrica Suppl, 88(432), pp. 61-64, Dec. 1999.

Doebler et al.; Continuous-flow, rapid lysis devices for biodefense nucleic acid diagnostic systems; Journal of the Association for Laboratory Automation; 14(3); pp. 119-125; Jun. 2009.

Dong et al.; Highly sensitive multiple microRNA detection based on flourescence quenching of graphene oxide and isothermal stranddisplacement polymerase reaction; Anal Chem; 84; pp. 4587-4593; Apr. 2012.

Dryden et al.; Integrated digital microfluidic platform for voltammetric analysis; Analytical Chemistry: 85(18); pp. 8809-8816; Sep. 2013.

Duffy et al.; Rapid prototyping of microfluidic systems in Poly (dimethylsiloxane), Anal. Chem., 70(23), pp. 4974-4984, Dec. 1998.

Edgar et al.; Capillary electrophoresis separation in the presence of an immiscible boundary for droplet analysis, Anal. Chem., 78(19), pp. 6948-6954 (author manuscript, 15 pgs.), Oct. 2006.

Egholm et al., PNA hybridizes to complementary oligonucleotides obeying the Watson-Crick hydrogen-bonding rules, Nature, 365(6446), pp. 566-568, Oct. 1993.

Egholm et al., Recognition of guanine and adenine in DNA by cytosine and thymine containing peptide nucleic acids (PNA), J. Am. Chem. Soc., 114(24), pp. 9677-9678; Nov. 1992.

Ehrmann; Polycystic ovary syndrome. New England Journal of Medicine; 352 (12); pp. 1223-1236; Mar. 2005.

Ekstrom et al.; Miniaturized solid-phase extraction and sample preparation for MALDI MS using a microfabricated integrated selective enrichment target, Journal of Proteome Research, 5(5), pp. 1071-1081, May 2006.

Ekstrom et al., Polymeric integrated selective enrichment target (ISET) for solid-phase-based sample preparation in MALDI-TOF MS, Journal of Mass Spectrometry, 42(11), pp. 1445-1452, Nov. 2007.

Ekstrom et al., On-chip microextraction for proteomic sample preparation of in-gel digests, Proteomics, 2(4), pp. 413-421, Apr. 2002.

El-Ali et al.; Cells on chips; Nature (2006) insight Review; 442(7101); pp. 403-411; Jul. 2006.

Fair; Digital microfluidics: Is a true lab-on-a-chip possible ?; Microfuid. Nanofluid.; 3(3); pp. 245-281; Jun. 2007.

Falk et al.; Measurement of Sex Steroid Hormones in Breast Adipocytes: Methods and Implications; Cancer Epidemiol Biomarkers Prev; 17(8); pp. 1891-1895; Aug. 2008.

Fan et al.; Cross-scale electric manipulations of cells and droplets by frequency-modulated dielectrophoresis and electrowetting; Lab Chip; 8(8); pp. 1325-1331; Aug. 2008.

Fan et al.; Electrically Programmable Surfaces for Configurable Patterning of Cells; Advanced Materials; 20(8); pp. 1418-1423; Apr. 2008.

Fan et al.; Integrated barcode chips for rapid, multiplexed analysis of proteins in microliter quanties of blood; Nature Biotechnology; 26(12); pp. 1373-1378; 15 pages (Author Manuscript); Dec. 2008.

Faure et al.; Improved electrochemical detection of a transthyretin synthetic peptide in the nanomolar range with a two-electrode system integrated in a glass/PDMS microchip; Lab on a Chip; 14(15); pp. 2800-2805, Aug. 2014.

Fobel et al.; DropBot: An open-source digital microfluidic control system with precise control of electrostatic driving force and instantaneous drop velocity measurement; Applied Physics Letters; 102(19); 193513 (5 pgs.); May 2013.

Foote et al., Preconcentration of proteins on microfluidic devices using porous silica membranes, Analytical Chemistry, 77(1), pp. 57-63, Jan. 2005.

Freire et al.; A practical interface for microfluidics and nanoelectrospray mass spectrometry, Electrophoresis, 29(9), pp. 1836-1843, May 2008.

Fridley et al., Controlled release of dry reagents in porous media for tunable temporal and spatial distribution upon rehydration, Lab Chip, 12(21), pp. 4321-4327 (author manuscript, 14 pgs.), Nov. 2012.

Fu et al., Controlled Reagent Transport in Disposable 2D Paper Networks, Lab. Chip, 10(7), pp. 918-920 (author manuscript, 9 pgs.), Apr. 2010.

Gao et al.; Unusual conformation of a 3'-thioformacetal linkage in a DNA duplex; J. Biomol. NMR; 4(1); pp. 17-34; Jan. 1994.

Gentili et al.; Analysis of free estrogens and their conjugates in sewage and river waters by solid-phase extraction then liquid chromatography-electrospray-tandem mass spectrometry. Chromatographia 56(1), pp. 25-32, Jul. 2002.

Gerasimova et al.; Fluorometric method for phenylalanine microplate assay adapted for phenylketonuria screening, Clinical Chemistry, 35(10), pp. 2112-2115, Oct. 1989.

Gong et al., All-Electronic Droplet Generation On-Chip With Real-Time Feedback Control For EWOD Digital Microfluidics, Lab Chip, 8(6), pp. 898-906 (author manuscript, 20 pgs.), Jun. 2008.

Gong et al.; Portable digital microfluidics platform with active but disposable lab-on-chip; 17th IEEE International Conference on Micro Electro Mechanical Systems; Maastricht, Netherlands; pp. 355-358; Jan. 24-29, 2004.

Gong et al., Two-dimensional digital microfluidic system by multilayer printed circuit board, 18th IEEE International Conference on Micro Electro Mechanical Systems (MEMS 2005); IEEE; pp. 726-729; Jan. 30-Feb. 3, 2005.

Goto et al.; Colorimetric detection of loop-mediated isothermal amplification reaction by using hydroxy naphthol blue; Biotechniques; 46(3); pp. 167-172; Mar. 2009.

Gottschlich et al.; Integrated microchip-device for the digestion, separation and postcolumn labeling of proteins and peptides, J. Chromatogr. B. 745(1), pp. 243-249, Aug. 2000.

Govindarajan et al., A low cost point-of-care viscous sample preparation device for molecular diagnosis in the developing world; an example of microfluidic origami, Lab Chip, 12(1), pp. 174-181, Jan. 2012.

Green et al.; Neonatal screening by DNA microarray: spots and chips, Nature Reviews Genetics, 6(2), pp. 147-151, Feb. 2005.

(56) References Cited

OTHER PUBLICATIONS

Hatch et al., Integrated preconcentration SDS-PAGE of proteins in microchips using photopatterned cross-linked polyacrylamide gels, Analytical Chemistry, 78(14), pp. 4976-4984, Jul. 2006.
He et al. (ed); Food microbiological inspection technology; Chapter 5: Modern food microbiological inspection technology; China Quality Inspection press; pp. 111-113; (English Translation included) Nov. 2013.
Henderson et al.; Estrogens as a cause of human cancer: The Richard and Hinda Rosenthal Foundation award lecture. Cancer Res, 48(2), pp. 246-253, Jan. 1988.
Hennequin et al.; Synthesizing microcapsules with controlled geometrical and mechanical properties with microfluidic double emulsion technology; Langmuir; 25(14); pp. 7857-7861; Jul. 2009.
Herdewijn et al.; 2'-5'-Oligoadenylates (2-5A) As Mediators of Interferon Action. Synthesis and Biological Activity of New 2-5A Analogues. E. De Clerq (ed.) Frontiers in Microbiology, 231-232, Springer, Dordrecht Jan. 1987.
Hertz et al.; Estrogen-progestogen combinations for contraception. Journal of the American Medical Association, 198(9), pp. 1000-1006, Nov. 1966.
Hong et al.; Three-dimensional digital microfluidic manipulation of droplets in oil medium; Scientific Reports; 5 (Article No. 10685); 5 pgs.; Jun. 2015.
Horn et al.; Oligonucleotides with alternating anionic and cationic phosphoramidate linkages: Synthesis and hybridization of stereo-uniform isomers; Tetrahedron Lett.; 37(6); pp. 743-746; Feb. 1996.
Hou et al.; Microfluidic devices for blood fractionation; Micromachines; 2(3); pp. 319-343; Jul. 20, 2011.
Huh et al.; Reversible Switching of High-Speed Air-Liquid Two-Phase Flows Using Electrowetting-Assisted Flow-Pattern Change, J. Am. Chem. Soc., 125, pp. 14678-14679; Dec. 2003.
Ihalainen et al; Application of paper-supported printed gold electrodes for impedimetric immunosensor development; Biosensors; 3(1); pp. 1-17; Mar. 2013.
Jacobson et al.; High-Speed Separations on a Microchip, Anal. Chem., 66(7), pp. 1114-1118, Apr. 1994.
Jacobson et al.; Precolumn Reactions with Electrophoretic Analysis Integrated on a Microchip, Anal. Chem., 66(23), pp. 4127-4132, Dec. 1994.
Jebrail et al., Combinatorial Synthesis of Peptidomimetics Using Digital Microfluidics, J. Flow Chem., 2(3), pp. 103-107; (online) Aug. 2012.
Jebrail et al., Let's get digital: digitizing chemical biology with microfluidics, Curr. Opin. Chem. Biol., 14(5), 574-581, Oct. 2010.
Jebrail et al., Synchronized synthesis of peptide-based macrocycles by digital microfluidics, Angew. Chem. Int. Ed. Eng., 49(46), pp. 8625-8629, Nov. 2010.
Jebrail et al., World-to-digital-microfluidic interface enabling extraction and purification of RNA from human whole blood, Analytical Chemistry, 86(8), pp. 3856-3862, Apr. 2014.
Jebrail et al.; A Solvent Replenishment Solution for Managing Evaporation of Biochemical Reactions in Air-Matrix Digital Microfluidics Devices, Lab on a Chip, 15(1), pp. 151-158; Jan. 2015.
Jebrail et al.; Digital Microfluidic Method for Protein Extraction by Precipitation; Analytical Chemistry; 81(1); pp. 330-335; Jan. 2009.
Jebrail et al.; Digital Microfluidics for Automated Proteomic Processing, Journal of Visualized Experiments, 33 (e1603), 5 pgs., Nov. 2009.
Jebrail et al.; Digital microfluidics: a versatile tool for applications in chemistry, biology and medicine; Lab Chip; 12 (14); pp. 2452-2463; Jul. 2012.
Jemere et al., An integrated solid-phase extraction system for sub-picomolar detection, Electrophoresis, 23(20), pp. 3537-3544, Oct. 2002.
Jenkins et al., The biosynthesis of carbocyclic nucleosides; Chem. Soc. Rev.; 24(3); pp. 169-176; Jan. 1995.
Jensen et al., Free-running enzymatic oligonucleotide synthesis for data storage applications; bioRxiv; 1:355719; 7 pages; Jan. 2018.

Jessome et al.; Ion Suppression: A Major Concern in Mass Spectrometry. LC-GC North America, 24(5), pp. 498-510, May 2006.
Jia et al.; Ultrasensitive detection of microRNAs by exponential isothermal amplification; Angew. Chem. Int. Ed. Engl.; 49(32); pp. 5498-5501; Jul. 2010.
Jung et al.; Hybridization of Alternating Cationic/Anionic Oligonucleotides to RNA Segments; Nucleosides & Nucleotides; 13(6-7); pp. 1597-1605; Jul. 1994.
Kaaks et al.; Postmenopausal serum androgens, oestrogens and breast cancer risk: The European prospective investigation into cancer and nutrition. Endocrine-Related Cancer,12(4), pp. 1071-1082, Dec. 2005.
Keng et al., Micro-chemical synthesis of molecular probes on an electronic microfluidic device,PNAS, 109(3), pp. 690-695; Jan. 2012.
Kiedrowski et al., Parabolic Growth of a Self-Replicating Hexadeoxynucleotide Bearing a 3'-5-Phosphoamidate Linkage; Angew. Chemie Intl. Ed.; 30(4); pp. 423-426; Apr. 1991.
Kim et al.; Automated digital microfluidic sample preparation for next-generation DNA sequencing; JALA; Journal of the Association for Laboratory Automation; 16(6); pp. 405-414; Dec. 2011.
Kim et al., A Microfluidic DNA Library Preparation Platform for Next-Generation Sequencing, PLoS One, 8(7), Article ID: e68988; 9 pgs., Jul. 2013.
Kim et al.; Microfabricated Monolithic Multinozzle Emitters for Nanoelectrospray Mass Spectrometry; Anal Chem; 79(10); pp. 3703-3707; May 2007.
Koster et al.; Drop-based microfluidic devices for encapsulation of single cells; Lab on a Chip; 8(7); pp. 1110-1115; Jul. 2008.
Kralj et al.; Integrated continuous microfluidic liquid-liquid extraction. Lab on a Chip, 7(2), pp. 256-263, Feb. 2007.
Kutter et al., Solid phase extraction on microfluidic devices, Journal of Microcolumn Separations, 12(2), pp. 93-97, Jan. 2000.
Kutter et al., Solvent—Programmed Microchip Open-Channel Electrochromatography, Analytical Chemistry, 70(15), pp. 3291-3297, Aug. 1998.
Labrie et al.; Androgen glucuronides, instead of testosterone, as the new markers of androgenic activity in women. The Journal of Steroid Biochemistry and Molecular Biology, 99(4-5), pp. 182-188, Jun. 2006.
Labrie; Intracrinology. Molecular and Cellular Endocrinology, 78(3), pp. C113-C118, Jul. 1991.
Lamar et al.; Serum sex hormones and breast cancer risk factors in postmenopausal women. Cancer Epidemiol Biomarkers Prev, 12(4), pp. 380-383, Apr. 2003.
Langevin et al., A rapid and unbiased method to produce strand-specific RNA-Seq libraries from small quantities of starting materiaRNA Biol., 10(4), pp. 502-515, (online) Apr. 2013.
Lawyer et al.; High-level expression, purification, and enzymatic characterization of full-length Thermus aquaticus DNA polymerase and a truncated form deficient in 5' to 3' exonuclease activity; Genomne Res; 2(4); pp. 275-287; May 1993.
Lawyer et al.; Isolation, characterization, and expression in *Escherichia coli* of the DNA polymerase gene from Thermus aquaticus; J. Biol. Chem.; 264; pp. 6427-6437; Apr. 1989.
Lebrasseur et al.; Two-dimensional electrostatic actuation of droplets using a single electrode panel and development of disposable plastic film card; Sensors and Actuators A; 136(1); pp. 368-386; May 2007.
Lee et al.; Electrowetting and electrowetting-on-dielectric for microscale liquid handling, Sens. Actuators A, 95(2), pp. 259-268, Jan. 2002.
Lee et al.; Removal of bovine serum albumin using solid-phase extraction with in-situ polymerized stationary phase in a microfluidic device; Journal of Chromatography A; 1187(1-2); pp. 11-17; Apr. 2008.
Lee et al.; Surface-Tension-Driven Microactuation Based on Continuous Electrowetting; J. Microelectromechanical Systems; 9(2); pp. 171-180; Jun. 2000.
Leriche et al.; Cleavable linkers in chemical biology; Bioorganic & Medicinal Chemistry; 20(2); pp. 571-582; Jan. 15, 2012.
Letsinger et al., Cationic oligonucleotides, J. Am. Chem. Soc., 110(13), pp. 4470-4471, Jun. 1988.

(56) References Cited

OTHER PUBLICATIONS

Letsinger et al., Effects of pendant groups at phosphorus on binding properties of d-ApA analogues, Nucl. Acids Res., 14(8), pp. 3487-3499, Apr. 1986.
Letsinger et al., Phosphoramidate analogs of oligonucleotides, J. Org. Chem., 35(11), pp. 3800-3803, Nov. 1970.
Lettieri et al., A novel microfluidic concept for bioanalysis using freely moving beads trapped in recirculating flows, Lab on a Chip, 3(1), pp. 34-39, Feb. 2003.
Levy et al.; Genetic screening of newborns, Annual Review of Genomics and Human Genetics, 1, pp. 139-177, Sep. 2000.
Li et al., A perspective on paper-based microfluidics: Current status and future trends, Biomicrofluidics, 6(1), pp. 011301 (13 pgs), Mar. 2012.
Li et al., Application of microfluidic devices to proteomics research: identification of trace-level protein digests and affinity capture of target peptides, Molecular & cellular Proteomics, 16(2), pp. 157-168, Feb. 2002.
Li et al., Paper-based microfluidic devices by plasma treatment, Anal. Chem., 80(23), pp. 9131-9134, Nov. 2008.
Li et al.; A Low-Cost and High resolution droplet position detector for an intelligent electrowetting on dielectric device; Journal of Lab. Automation 2015; 20(6); pp. 663-669; Dec. 2015.
Li et al.; One-step ultrasensitive detection of microRNAs with loop-mediated isothermal amplification (LAMP); Chem Commun; 47(9); pp. 2595-2597; Mar. 2011.
Li et al.; Test structure for characterizing low voltage coplanar EWOD system; IEEE Transaction on Semiconductor Manufacturing; IEEE Service Center; Piscataway, NJ.; 22(1); pp. 88-95; Feb. 4, 2009.
Liana et al.; Recent Advances in Paper-Based Sensors; Sensors; 12(9); pp. 11505-11526; Aug. 2012.
Link et al.; Electric Control of Droplets in Microfluidic Devices; Angew Chem Int Ed Engl; 45(16); pp. 2556-2560; Apr. 2006.
Liu et al., Three-dimensional paper microfluidic devices assembled using the principles of origami, JACS, 133(44), pp. 17564-17566, Nov. 2011.
Liu et al.; Attomolar ultrasensitive microRNA detection by DNA-scaffolded silver-nanocluster probe based on isothermal amplification; Anal Chem; 84(12); pp. 5165-5169; Jun. 2012.
Lizardi et al.; Mutation detection and single-molecule counting using isothermal rolling-circle amplification; Nat. Genet.; 19(3); pp. 225-232; Jul. 1998.
Locascio et al.; Surface chemistry in polymer microfluidic systems; in Lab-on-a-Chip; Elsevier Science; 1st Ed.; pp. 65-82; Oct. 2003.
Loeber; Neonatal screening in Europe; the situation in 2004, Journal of Inherited Metabolic Disease, 30(4), pp. 430-438, Aug. 2007.
Lohman et al.; Efficient DNA ligation in DNA-RNA hybrid helices by Chlorella virus DNA ligase; Nucleic Acids Research; 42(3); pp. 1831-1844; Nov. 2013.
Luk et al.; Pluronic Additives: A Solution to Sticky Problems in Digital Microfluidics, Langmuir, 24(12), pp. 6382-6389, Jun. 2008.
Luk et al; A digital microfluidic approach to proteomic sample processing; Analytical Chemistry; 81(11); pp. 4524-4530; Jun. 2009.
Mag et al., Synthesis and selective cleavage of an oligodeoxynucleotide containing a bridged internucleotide 5'-phosphorothioate linkage, Nucleic Acids Res., 19(7), pp. 1437-1441, Apr. 1991.
Mais et al.; A solvent replenishment solution for managing evaporation of biochemical reactions in air-matrix digital microfluidics devices; Lab on a Chip; 15(1); pp. 151-158; Jan. 2015.
Makamba et al.; Surface modification of poly(dimethylsiloxane) microchannels; Electrophoresis; 24(21); pp. 3607-3619, Nov. 2003.
Malloggi et al.; Electrowetting—A versatile tool for controlling microdrop generation, Eur. Phys. J. E, 26(1), pp. 91-96, May 2008.
Mandl et al.; Newborn screening program practices in the United States: notification, research, and consent, Pediatrics, 109(2), pp. 269-273, Feb. 2002.

Maroney et al.; A Rapid, quantitative assay for direct detection of microRNAs and other small RNAs using splinted ligation; RNA; 13(6); pp. 930R936; Jun. 2007.
Maroney et al.; Direct detection of small RNAs using splinted ligation; Nat. Protocols3(2); pp. 279-287; Jan. 2008.
Marre et al.; Synthesis of micro and nanostructures in microfluidic systems; Chemical Society Reviews; 39(3); pp. 1183-1202; Mar. 2010.
Martinez et al., Simple Telemedicine for Developing Regions: Camera Phones and Paper-Based Microfluidic Devices for Real-Time, Off-Site Diagnosis, Anal. Chem., 80(10), pp. 3699-3707, May 2008.
Martinez et al., Three-dimensional microfluidic devices fabricated in layered paper and tape, PNAS, 105(50), pp. 19606-19611, Dec. 2008.
Martinez et al.; Patterned paper as a platform for inexpensive low-volume portable bioassays, Angewandte Chemie, 46(8), pp. 1318-1320, Feb. 2007.
Martinez-Sanchez et al.; MicroRNA Target Identification—Experimental Approaches; Biology; 2; pp. 189-205; Jan. 2013.
Matern et al.; Reduction of the false-positive rate in newborn screening by implementation of MS/MS-based second-tier tests: the Mayo Clinic experience (2004-2007), Journal of Inherited Metabolic Disease, 30(4), pp. 585-592, Aug. 2007.
Mauney, Thermal Considerations for Surface Mount Layouts, in Texas Instruments Portable Power Supply Design Seminar, 16 pgs., 2006.
Mega; Heterogenous ion-exchange membranes RALEX; 3 pgs.; retrieved Mar. 1, 2016 from the internet: http://www.mega.cz/heterogenous-ion-exchange-membranes-ralex.html.
Meier et al., The photochemistry of stilbenoid compounds and their role in materials technology, Chem. Int. Ed. Engl., 31(11), pp. 1399-1420, Nov. 1992.
Mellors et al.; Fully Integrated Glass Microfluidic Device for Performing High-Efficiency Capillary Electrophoresis and Electrospray Ionization Mass Spectrometry, Analytical Chemistry, 80(18), pp. 6881-6887 (Author Manuscript, 18 pgs.), Sep. 2008.
Michigan Dept. of Community Health; Specimen collection procedure from Michigan Newborn Screening Program, 37 pgs., (retrieved Feb. 9, 2017 online: http://web.archive.org/web/20100715000000*/http://www.michigan.gov/documents/Bloodco2_60773_7.pdf) Jul. 2009.
Miller et al.; A digital microfluidic approach to homogeneous enzyme assays, Anal. Chem., 80(5), pp. 1614-1619, Mar. 2008.
Millington et al.; Digital Microfluidics: A Future Technology in the Newborn Screening Laboratory?, Seminars in Perinatology, 34(2), pp. 163-169 (Author Manuscript, 14 pgs.), Apr. 2010.
Millington et al.; Digital Microfluidics: A novel platform for multiplexed detection of LSDs with potential for newborn screening (conference presentation); Oak Ridge Conference; 15 pgs.; 2009.
Millington et al.; Tandem mass spectrometry: a new method for acylcarnitine profiling with potential for neonatal screening for inborn errors of metabolism, Journal of Inherited Metabolic Disease, 13(3), pp. 321ý324, May 1990.
Millington et al.; The Analysis Of Diagnostic Markers Of Genetic Disorders In Human Blood And Urine Using Tandem Mass Spectrometry With Liquid Secondary Ion Mass Spectrometry, International Journal of Mass Spectrometry, 111, pp. 211-228, Dec. 1991.
Miralles et al.; A Review of Heating and Temperature Control in Microfluidic Systems: Techniques and Applications; Diagnostics; 3; pp. 33-67; Jan. 2013.
Mitchell et al.; Circulating microRNAs as stable blood-based markers for cancer detection; Proc Nat Acad Sci; 105(30); pp. 10513-10518; Jul. 2008.
Moon et al.; An integrated digital microfluidic chip for multiplexed proteomic sample preparation and analysis by MALDI-MS. Lab Chip, 6(9), pp. 1213-1219, Sep. 2006.
Moqadam et al.; The Hunting of Targets: Challenge in miRNA Research; Leukemia; 27(1); pp. 16-23; Jan. 2013.
Mousa et al.; Droplet-scale estrogen assays in breast tissue, blood, and serum, Science Translational Medicine, 1(1), 6 pgs., Oct. 2009.
Murran et al.; Capacitance-based droplet position estimator for digital microfluidic devices; Lab Chip; 12(11); pp. 2053-2059; May 2012.

(56) References Cited

OTHER PUBLICATIONS

Nakamura et al.; Simple and accurate determination of CYP2D6 gene copy number by a loop-mediated isothermal amplification method and an electrochemical DNA chip; Clinica Chimica Acta; 411(7-8); pp. 568-573; Apr. 2010.

Nelson et al., Incubated protein reduction and digestion on an EWOD digital microfluidic chip for MALDI-MS, Analytical Chemistry, 82(23), pp. 9932-9937, Dec. 2010.

Newborn Screening Ontario, The newborn screening ontario unsatisfactory sample indicator (educational resource), 3 pgs., retrieved online: https:/www.newbornscreening.on.ca/en/health-care-providers/submitters/report-cards/nso_unsatisfatory_sample_indicator_jan_2017, (web address was available to applicant(s) at least as of Jan. 2010).

Ng et al., Digital microfluidic magnetic separation for particle-based immunoassays, Anal. Chem., 84(20), 8805-8812, Oct. 2012.

Nilsson et al.; RNA-templated DNA ligation for transcript analysis; Nucl. Acid Res.; 29(2); pp. 578-581; Jan. 2001.

Njiru; Loop-Mediated Isothermal Amplification Technology: Towards Point of Care Diagnostics; PLoS; 6(6); pp. e1572 (4 pgs.); Jun. 2012.

Notomi et al.; Loop-mediated isothermal amplification of DNA; Nucleic Acid Research; 28(12); p. e63 (7 pgs.); Jun. 2000.

Okubo et al.; Liquid-liquid extraction for efficient synthesis and separation by utilizing micro spaces. Chemical Engineering Science, 63(16), pp. 4070-4077, Aug. 2008.

Oleschuk et al., Trapping of bead-based reagents within microfluidic systems: On-chip solid-phase extraction and electrochromatography, Analytical Chemistry, 72(3), pp. 585-590, Feb. 2000.

Padilla et al.; Newborn screening in the Asia Pacific region, Journal of Inherited Metabolic Disease, 30(4), pp. 490-506, Aug. 2007.

Palluk et al.; De novo DNA synthesis using polymerase-nucleotide conjugates; Nature biotechnology; 36(7); pp. 645-650; Jun. 18, 2018.

Paik et al., Coplanar digital microfluidics using standard printed circuit board processes, in Proceedings 9th Int'l Conf Miniaturized Systems for Chemistry and Life Sciences (MicroTAS 2005), Boston, MA, USA, pp. 566-568, Oct. 9-13, 2005.

Paneri et al.; Effect of change in ratio of electrode to total pitch length in EWOD based microfluidic system; InComputer Applications and Industrial Electronics (ICCAIE); 2010 International Conference; pp. 25-28; Dec. 5, 2010.

Parida et al.; Rapid detection and differentiation of Dengue virus serotypes by a real-time reverse transcription-loop-mediated isothermal amplification assay; J Clinical Microbiology; 43(6); pp. 2895-2903; Jun. 2005.

Pauwels et al., Biological-Activity of New 2-5a Analogs, Chemica Scripta, 26 (1), pp. 141-145, Mar. 1986.

Peltonen et al.; Printed electrodes on tailored paper enable electrochemical functionalization of paper; TAPPI Nanotechnology Conference; Espoo, Finland; 20 pgs.; Sep. 2010.

Peterschmitt et al.; Reduction of false negative results in screening of newborns for homocystinuria, New England Journal of Medicine, 341(21), 1572-1576, Nov. 1999.

Petersen et al., On-chip electro membrane extraction, Microfluidics and Nanofluidics, 9(4), pp. 881-888, Oct. 2010.

Pitt et al.; Hormone replacement therapy for osteoporosis. Lancet, 335 (8695), p. 978, Apr. 1990.

Pollack et al.; Electrowetting-based actuation of droplets for integrated microfluidics; Lab on a Chip; 2(2); pp. 96-101; May 2002.

Pollack et al.; Electrowetting-based actuation of liquid droplets for microfluidic applications, Appl. Phys. Lett., 77(11), pp. 1725-1726, Sep. 2000.

Provincial Health Services Authority (British Columbia Perinatal Health Program), Perinatal Services BC Neonatal Guideline 9: Newborn Screening. 29 pgs., (retrieved Feb. 9, 2017 online: http://www.perinatalservicesbc.ca/health-professionals/guidelines-standards/newborn) guideline revised: Dec. 2010.

Rahhal et al.; The impact of assay sensitivity in the assessment of diseases and disorders in children. Steroids, 73(13), pp. 1322-1327, Dec. 2008.

Rashad; Clinical applications of tandem mass spectrometry: ten years of diagnosis and screening for inherited metabolic diseases, Journal of Chromatography B: Biomedical Sciences and Applications, 758(1), pp. 27-48, Jul. 2001.

Rashed et al.; Diagnosis of inborn errors of metabolism from blood spots by acylcarnitines and amino acids profiling using automated electrospray tandem mass spectrometry, Pediatric Research, 38(3), 324-331, Sep. 1995.

Rawls, Optimistic About Antisense: Promising clinical results and chemical strategies for further improvements delight antisense drug researchers; Chemical & Engineering News; 75(22); pp. 35-39; Jun. 2, 1997.

Ren et al., Automated on-chip droplet dispensing with volume control by electro-wetting actuation and capacitance metering, Sens. Actuator B Chem., 98(2-3), pp. 319-327, Mar. 2004.

Ren et al.; Design and testing of an interpolating mixing architecture for electrowetting-based droplet-on-chip chemical dilution; 12th International Conference on Transducers, Solid-State Sensors, Actuators and Microsystems; vol. 2; Boston, MA, USA; pp. 619-622; Jun. 8-12, 2003.

Ro et al.; Poly (dimethylsiloxane) microchip for precolumn reaction and micellar electrokinetic chromatography of biogenic amines, Electrophoresis, 23(7-8), pp. 1129-1137, Apr. 2002.

Roman et al.; Fully integrated microfluidic separations systems for biochemical analysis, J. Chromatogr. A, 1168(1-2), pp. 170-188, Oct. 2007.

Roman et al.; Sampling and Electrophoretic Analysis of Segmented Flow Streams in a Microfluidic Device, Anal. Chem., 80(21), pp. 8231-8238 (author manuscript, 19 pgs.), Nov. 2008.

Sabourin et al.; Interconnection blocks: a method for providing reusable, rapid, multiple, aligned and planar microfluidic interconnections; Journal of Micromechanics and Microengineering; 19(3); 10 pages; doi:10.1088/0960-1317/19/3/035021; Feb. 18, 2009.

Sadeghi et al.; On Chip Droplet Characterization: A Practical, High-Sensitivity Measurement of Droplet Impedance in Digital Microfluidics; Anal. Chem.; 84(4); pp. 1915-1923; Feb. 2012.

Sahai et al.; Newborn screening, Critical Reviews in Clinical Laboratory Sciences, 46(2), pp. 55-82, (online) Mar. 2009.

Samsi et al.; A Digital Microfluidic Electrochemical Immunoassay; Lab On A Chip; 14(3); pp. 547-554; Feb. 2014.

Sanghvi & Cook (Ed.); Carbohydrate Modifications in Antisense Research; Chapters 2 and 3, American Chemical Society, Washington DC; (207th National Meeting of the American Chemical Society Mar. 13-17, 1994, San Jose, CA); Dec. 1994.

Sanghvi & Cook (Ed.); Carbohydrate Modifications in Antisense Research; Chapters 6 and 7, American Chemical Society, Washington DC; (207th National Meeting of the American Chemical Society Mar. 13-17, 1994, San Jose, CA); Dec. 1994.

Santen et al.; Superiority of gas chromatography/tandem mass spectrometry assay (GC/MS/MS) for estradiol for monitoring of aromatase inhibitor therapy. Steroids. 72(8), pp. 666-671, Jul. 2007.

Sasano et al.; From Endocrinology to Intracrinology. Endocr Pathol, 9(1), pp. 9-20, Spring 1998.

Satoh et al.; Electrowetting-based valve for the control of the capillary flow, J. Appl. Phys., 103(3), 034903, Feb. 2008.

Satoh et al.; On-chip microfluidic transport and mixing using electrowetting and incorporation of sensing functions, Anal. Chem., 77(21), pp. 6857-6863, Nov. 2005.

Sawai et al., Synthesis and properties of oligoadenylic acids containing 2?-5? phosphoramide linkage, Chem. Lett., 13(5), pp. 805-808, May 1984.

Schertzer et al.; Using capacitance measurements in EWOD devices to identify fluid composition and control droplet mixing; Sens. Actuators B; 145(1); pp. 340-347; Mar. 2010.

Scriver_Commentary; A Simple Phenylalanine Method For Detecting Phenylketonuria in Large Populations Of Newborn Infants by Guthrie et al., Pediatrics, 32(3), 338-343, Sep. 1963.

Shah et al., On-demand droplet loading for automated organic chemistry on digital microfluidics, Lab Chip, 13(14), pp. 2785-2795, Jul. 2013.

(56) References Cited

OTHER PUBLICATIONS

Shamsi et al; A digital microfluidic electrochemical immunoassay; Lab on a Chip; 14(3); pp. 547-554; (year of pub. sufficiently earlier than effective US filing date and any foreign priority date) 2014.

Shih et al., A feedback control system for high-fidelity digital microfluidics, Lab Chip, 11(3), pp. 535-540, Feb. 2011.

Simpson et al.; Estrogen—the Good, the Bad, and the Unexpected. Endocr Rev, 26(3), pp. 322-330; May 2005.

Sinha et al., A Versatile Automated Platform for Micro-scale Cell Stimulation Experiments, J. Vis. Exp., e50597, 8 pgs., Aug. 2013.

Sinton et al.; Electroosmotic velocity profiles in microchannels, Colloids Surf. A, 222(1-3), pp. 273-283, Jul. 2003.

Skendzel, Rubella immunity: Defining the level of protective antibody, Am. J. Clin. Pathol., 106(2), 170-174, Aug. 1996.

Smith et al; Diagnosis and Management of Female Infertility. Journal of the American Medical Association 290(13), pp. 1767-1770, Oct. 2003.

Sooknanan et al., Nucleic Acid Sequence-Based Amplification, Ch. 12; Molecular Methods for Virus Detection (1st Ed.), Academic Press, Inc., pp. 261-285; Jan. 1995.

Sprinzl et al., Enzymatic incorporation of ATP and CTP analogues into the 3' end of tRNA, Eur. J. Biochem., 81(3), pp. 579-589, Dec. 1977.

Srinivasan et al.; An integrated digital microfluidic lab-on-a-chip for clinical diagnostics on human physiological fluids, Lab Chip, 4(4), pp. 310-315, Aug. 2004.

Stanczyk et al.; Standardization of Steroid Hormone Assays Why, How, and When?, Cancer Epidemiol Biomarkers Prev, 16(9), pp. 1713-1719, Sep. 2007.

Steckl et al.; Flexible Electrowetting And Electrowetting On Flexible Substrates; Proc. SPIE 7956; Advances in Display Technologies; and E-papers and Flexible Displays; 795607 (6 pgs.); Feb. 2011.

Stegink et al.; Plasma amino acid concentrations and amino acid ratios in normal adults and adults heterozygous for phenylketonuria ingesting a hamburger and milk shake meal, American Journal of Clinical Nutrition, 53(3), pp. 670-675, Mar. 1991.

Sun et al.; Rapid and direct microRNA quantification by an enzymatic luminescence assay; (author manuscript; 17 pgs.) Analytical Biochemistry; 429(1); pp. 11-17; Oct. 2012.

Svoboda et al.; Cation exchange membrane integrated into a microfluidic device; Microelectronic Engineering; 86; pp. 1371-1374; Apr.-Jun. 2009.

Szarewski et al.; Contraception. Current state of the art. British Medical Journal, 302(6787), pp. 1224-1226, May 1991.

Szymczak et al.; Concentration of Sex Steroids in Adipose Tissue after Menopause. Steroids, 63(5-6), pp. 319-321, May/Jun. 1998.

Tachibana et al.; Application of an enzyme chip to the microquantification of L-phenylalanine, Analytical Biochemistry, 359(1), pp. 72-78, Dec. 2006.

Tan et al.; A lab-on-a-chip for detection of nerve agent sarin in blood; Lab Chip; 8(6); pp. 885-891; Jun. 2008.

Tang et al.; Mechano-regulated surface for manipulating liquid droplets; Nature Communications; 10 pages; DOI: 10.1038/ncomms14831; ; Apr. 4, 2017.

Teh et al.; Droplet microfluidics, Lab Chip, 8(2), pp. 198-220, Feb. 2008.

Theberge et al.; Microdroplets in microfluidics: an evolving plarform for discoveries in chemistry and biology; Angewandte Chemie International Edition; 49(34); pp. 5846-5868; Aug. 2010.

Therrell et al.; Newborn screening in North America, Journal of Inherited Metabolic Disease, 30(4), pp. 447-465, Aug. 2007.

Tian et al., Printed two-dimensional micro-zone plates for chemical analysis and ELISA, Lab on a Chip, 11(17), pp. 2869-2875, Sep. 2011.

Tobjörk et al., IR-sintering of ink-jet printed metal-nanoparticles on paper, Thin Solid Films, 520(7), pp. 2949-2955, Jan. 2012.

Tomita et al.; Loop-mediated isothermal amplification (LAMP) of gene sequences and simple visual detection of products; Nature Protocols; 3(5); pp. 877-882; (online) Apr. 2008.

Torkkeli; Droplet microfluidics on a planar surface; VTT Technical Research Centre of Finland; Publications 504; 214 pages (Dissertation); Oct. 2003.

Turgeon et al.; Combined Newborn Screening for Succinylacetone, Amino Acids, and Acylcarnitines in Dried Blood Spots, Clinical Chemistry, 54(4), pp. 657-664, Apr. 2008.

Udenfriend et al.; Fluorescamine: a reagent for assay of amino acids, peptides, proteins, and primary amines in the picomole range, Science, 178(4063), pp. 871-872, Nov. 1972.

Unger et al.; Monolithic microfabricated valves and pumps by multilayer soft lithography, Science, 288(5463), pp. 113-116, Apr. 2000.

Univ. of Maryland—Baltimore Washington Medical Center; Plasma amino acids, 6 pgs., retrieved Feb. 10, 2017 from: http://www.mybwmc.org/library/1/003361, Web address available to applicant(s) at least as of Jan. 2010.

Verkman; Drug Discovery In Academia; Am J Physiol Cell Physiol; 286(3); pp. C465-C474; Feb. 2004.

Walker et al.; A Chemiluminescent DNA Probe Test Based on Strand Displacement Amplification (Chapter 15); Molecular Methods for Virus Detection (1st Ed.), Academic Press, Inc., pp. 329-349; Jan. 1995.

Walker et al.; A passive pumping method for microfluidic devices, Lab Chip, 2(3), pp. 131-134, Aug. 2002.

Wang et al., Paper-based chemiluminescence ELISA: lab-on-paper based on chitosan modified paper device and, Biosens. Bioelectron., 31(1), pp. 212-218, Jan. 2012.

Wang et al., Simple and covalent fabrication of a paper device and its application in sensitive chemiluminescence immunoassay, Analyst, 137(16), pp. 3821-3827, Aug. 2012.

Wang et al.; An integrated microfluidic device for large-scale in situ click chemistry screening; Lab on a Chip; 9(16); 9(16); pp. 2281-2285; 9 pages (Author Manuscript); Aug. 2009.

Wang et al.; Highly sensitive detection of microRNAs based on isothermal exponential amplification-assisted generation of catalytic G-quadruplexDNAzyme; Biosensors and Bioelectronics, 42; pp. 131-135; Apr. 2013.

Washburn et al.; Large-scale analysis of the yeast proteome by multidimensional protein identification technology, Nat. Biotechnol., 19(3), pp. 242-247, Mar. 2001.

Watson et al.; Multilayer hybrid microfluidics: a digital-to-channel interface for sample processing and separations; Anal. Chem.; 82(15); pp. 6680-6686; Aug. 2010.

Wheeler et al.; Electrowetting-Based Microfluidics for Analysis of Peptides and Proteins by Matrix-Assisted Laser Desorption/Ionization Mass Spectrometry; Anal Chem; 76(16); pp. 4833-4838; Aug. 2004.

Wheeler; Chemistry. Putting electrowetting to work; Science; 322(5901); pp. 539-540; Oct. 2008.

Wlodkowic et al.; Tumors on chips: oncology meets microfluidics; Current opinion in Chemical Biology; 14(5); pp. 556-567; Oct. 2010.

Wu et al.; Design, Simulation and Fabrication of Electrowetting-Based Actuators for Integrated Digital Microfluidics; Proceedings of the 1st IEEE International Conference on Nano/Micro Engineered and Molecular Systems; Zhuhai, China; pp. 1097-1100; Jan. 18-21, 2006.

Wu et al.; Electrophoretic separations on microfluidic chips, J. Chromatogr. A, 1184(1-2), pp. 542-559, Mar. 2008.

Yan et al., A microfluidic origami electrochemiluminescence aptamerdevice based on a porous Au-paper electrode and a phenyleneethynylene derivative, Chem. Commun. (Camb), 49(14), pp. 1383-1385, Feb. 2013.

Yan et al., Paper-based electrochemiluminescent 3D immunodevice for lab-on-paper, specific, and sensitive point-of-care testing, Chem.—Eur. J., 18(16), pp. 4938-4945, Apr. 2012.

Yi et al.; Spangler et al., Eds; Channel-to-droplet extractions for on-chip sample preparation, in Proceedings of Solid-State Sensor, Actuator and Microsystems Workshop, pp. 128-131, Jun. 2006.

Yin et al.; One-step, multiplexed fluorescence detection of microRNAs based on duplex-specific nuclease signal amplification; J. American Chem. Soc.; 134(11); pp. 5064-5067; Mar. 2012.

(56) References Cited

OTHER PUBLICATIONS

Yoon et al.; Preventing Biomolecular Adsorption in Electrowetting-Based Biofluidic Chips; Anal Chem; 75; pp. 5097-5102; Aug. 2003.
Yoon; Open-Surface Digital Microfluidics; The Open Biotechnology Journal; 2(1); pp. 94-100; Apr. 2008.
Young et al.; Calculation of DEP and EWOD Forces for Application in Digital Microfluidics, J. Fluids Eng., 130(8), pp. 081603-1-081603-9, Jul. 2008.
Yu et al., Monolithic porous polymer for on-chip solid-phase extraction and preconcentration prepared by photoinitiated in situ polymerization within a microfluidic device, Analytical Chemistry , 73(21), pp. 5088-5096, Nov. 2001.
Yu et al., Preparation of monolithic polymers with controlled porous properties for microfluidic chip applications using photoinitiated free-radical polymerization, Journal of Polymer Science, Part A: Polymer Chemistry, 40(6), pp. 755-769, Mar. 2002.
Yu et al.; A plate reader-compatible microchannel array for cell biology assays; Lab Chip; 7(3); pp. 388-391; Mar. 2007.
Yu et al.; Microfabrication of a digital microfluidic platform integrated with an on-chip electrochemical cell; Journal of Micromechanics and Microrgineering: 23(9); pp. 10 pages; doi: 10.1088/0960-1317/23/9/095025; Aug. 2013.
Yu et al.; Microfabrication of a digital microfluidic platform integrated with an on-chip electrochemical cell; Journal of Micromechanics and Microengineering: 23(9); doi: 10.1088/0960-1317/23/9/095025, 10 pages; Aug. 28, 2013.
Yu et al.; Parallel-plate lab-on-chip electrochemical analysis; Journal of Micromechanics and Microengineering: 24(1); 7 pages; doi: 10.1088/0960-1317/24/1/015020; Dec. 16, 2013.
Yue; Undergraduate Chemistry experiment (11); Hunan Normal University Press; First Edition; p. 96; (Machine Translation included); Oct. 2008.
Yung et al.; Micromagnetic-microfluidic blood cleansing devices; Lab on a Chip; 9(9); pp. 1171-1177; May 2009.
Zaffanello et al.; Multiple positive results during a neonatal screening program: a retrospective analysis of incidence, clinical implications and outcomes, Journal of Perinatal Medicine, 33(3), pp. 246-251, May 2005.
Zhang et al.; Multiplexed detection of microRNAs by tuning DNA-scaffolded silver nanoclusters; Analyst; 138(17); pp. 4812-4817; Sep. 2013.
Zhang et al.; The permeability characteristics of silicone rubber; In Proceedings of 2006 SAMPE Fall Technical Conference; 10 pages; Nov. 6, 2006.
Zhao et al., Lab on Paper, Lab Chip, 8(12), pp. 1988-1991, Dec. 2008.
Znidarsic-Plazl et al.; Steroid extraction in a microchannel system—mathematical modelling and experiments. Lab Chip, 7(7), pp. 883-889, Jul. 2007.
Zucker; Mfold Web Server for Nucleic Acid Folding and Hybridization Prediction; Nucleic Acid Research ; 31(13); pp. 3406-3415; Jul. 2003.
Zytkovicz et al.; Tandem mass spectrometric analysis for amino, organic, and fatty acid disorders in newborn dried blood spots: a two-year summary from the New England Newborn Screening Program, Clinical Chemistry, 47(11), pp. 1945-1955, Nov. 2001.
Tecan; Freedom EVO; 16 pages; retrieved from the internet: https(//instruments.cz/wp-content/uploads/2018/04/EVO.pdf) Oct. 4, 2023.
Jebrail et al.; U.S. Appl. No. 18/451,828 entitled "Methods of mechanical microfluidic manipulation," filed Aug. 17, 2023.
Soto-Moreno et al.; U.S. Appl. No. 17/728,952 entitled "Digital microfluidics devices and methods of using them," filed Apr. 25, 2022.
Soto-Moreno et al.; U.S. Appl. No. 17/775,373 entitled "Digital microfluidics systems, apparatus and method of using them," filed May 9, 2022.
Davoust et al.; Evaporation rate of drop arrays within a digital microfluidic system; Sensors and Actuators B Chemical; 189; pp. 157-164; Dec. 2013.
Soto-Moreno et al.; U.S. Appl. No. 17/434,531 entitled "Digital microfluidics devices and methods of using them," filed Aug. 27, 2021.
Soto-Moreno et al.; U.S. Appl. No. 17/630,048 entitled "Digital microfluidics devices and methods of use thereof," filed Jan. 25, 2022.
Davoust et al.; Evaporation Rate of Drop Arrays within a Digital Microsystem; Procedia Engineering; vol. 47; pp. 1-4; Jan. 1, 2012.
Nge et al.; Advances in microfluidic materials, functions, integration, and applications. Chemical reviews; 113(4); pp. 2550-2583; Apr. 10, 2013.
Jebrail et al.; U.S. Appl. No. 17//967,671 entitled "Evaporation Management In Digital Mecrofluidic Devices," filed Oct. 17, 2022.
Soto-Moreno et al.; U.S. Appl. No. 18/064,893 entitled "Digital microfluidics devices and methods of use thereof," filed Dec. 12, 2022.
Jebrail et al.; U.S. Appl. No. 18/528,671 entitled "Microfluidic devices and methods," filed Dec. 4, 2023.
Jebrail et al.; U.S. Appl. No. 18/568,534 entitled "Apparatuses and methods for digital microfluidics and micro-electroporation," filed Dec. 8, 2023.
Jebrail et al.; U.S. Appl. No. 18/402,701 entitled "Sequencing by synthesis using mechanical compression," filed Jan. 2, 2024.
Jebrail et al.; U.S. Appl. No. 18/416,693 entitled "Evaporation management in digital microfluidic devices," filed Jan. 18, 2024.
Ratcharak et al.; Surface coating with poly (trifluoroethyl methacrylate) through rapid expansion of supercritical CO2 solutions; The Journal of Supercritical Fluids; vol. 89; pp. 106-112; May 1, 2014.
merriam-webster.com; Replenish (definition); 11 pages; retrieved from the internet (https://www.merriam-webster.com/dictionary/replenish) on Jul. 22, 2024.
Jebrail et al.; U.S. Appl. No. 18/642,774 entitled "Control of evaporation in digital microfluidics," filed Apr. 22, 2024.
Jebrail et al.; U.S. Appl. No. 18/766,551 entitled "Microfluidic two-dimensional capillary manipulation devices and methods," filed Jul. 8, 2024.

\* cited by examiner

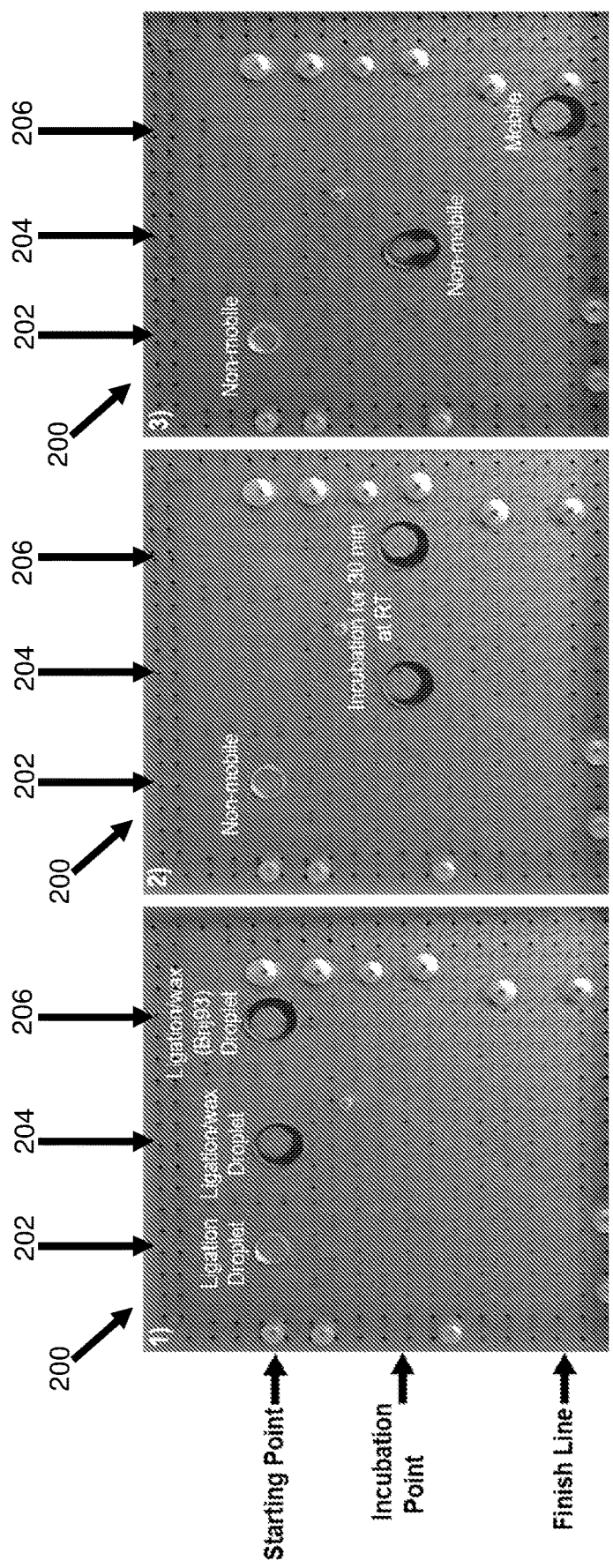

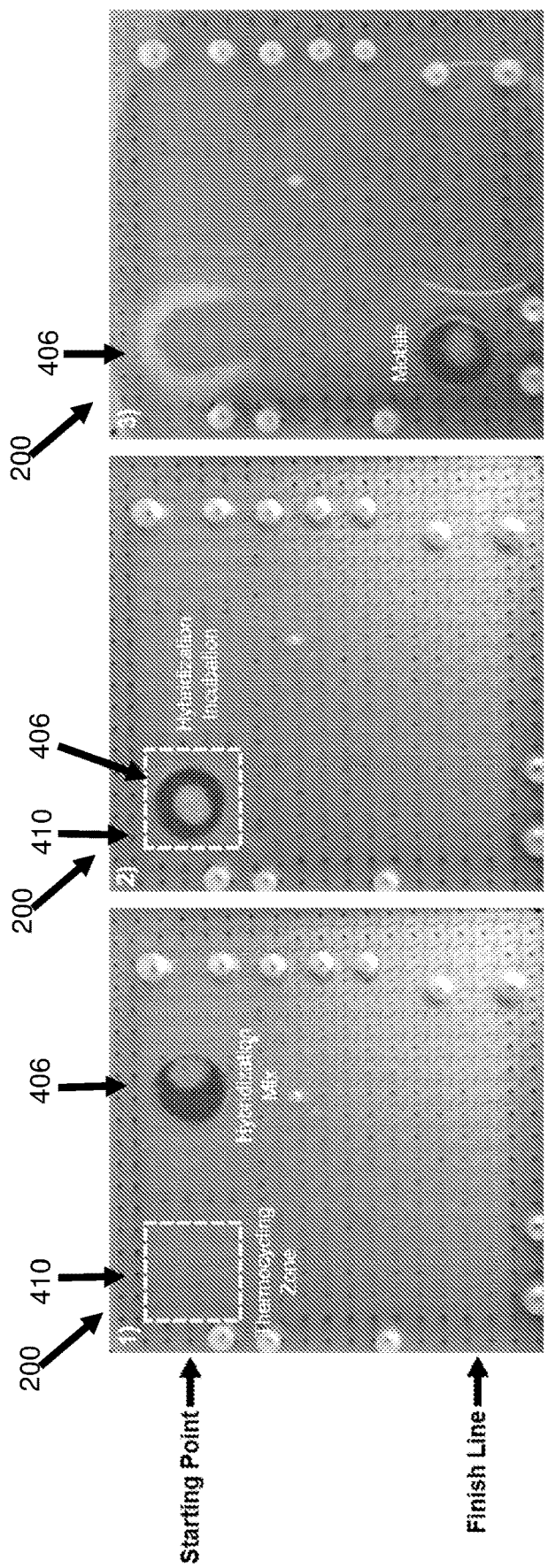

NONFOULING COMPOSITIONS AND METHODS FOR MANIPULATING AND PROCESSING ENCAPSULATED DROPLETS

CROSS REFERENCE TO RELATED APPLICATIONS

This patent application claims priority to U.S. Provisional Patent Application No. 62/799,734, filed on Jan. 31, 2019 (titled "NON FOULING COMPOSITIONS AND METHODS FOR MANIPULATING AND PROCESSING ENCAPSULATED DROPLETS"), which is herein incorporated by reference in its entirety.

This patent application may be related to International Application No. PCT/US2018/026095, titled DIGITAL MICROFLUIDIC APPARATUSES AND METHODS FOR MANIPULATING AND PROCESSING ENCAPSULATED DROPLETS," filed on Apr. 4, 2018; U.S. provisional patent applications No. 62/481,488, titled "DIGITAL MICROFLUIDICS APPARATUSES AND METHODS FOR MANIPULATING AND PROCESSING ENCAPSULATED DROPLETS," and filed on Apr. 4, 2017; U.S. provisional patent application No. 62/553,743, titled "DIGITAL MICROFLUIDICS DEVICES AND METHODS OF USING THEM," filed on Sep. 1, 2017; and U.S. provisional patent application No. 62/557,714, titled "DIGITAL MICROFLUIDICS DEVICES AND METHODS OF USING THEM," filed on Sep. 12, 2017, each of which is herein incorporated by reference in its entirety.

This patent application may be related to U.S. patent application Ser. No. 15/579,455, titled "AIR-MATRIX DIGITAL MICROFLUIDICS APPARATUSES AND METHODS FOR LIMITING EVAPORATION AND SURFACE FOULING," filed on Jun. 6, 2016, which claimed priority to U.S. Provisional Application 62/171,756 entitled, "DEVICE AND METHODS FOR LIMITING EVAPORATION AND SURFACE FOULING," filed on Jun. 5, 2015, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Compositions for use within air-matrix electrokinetic devices including air-matrix digital microfluidic (DMF) apparatuses and methods for manipulating and processing encapsulated droplets using same are described herein. These compositions may further be advantageously utilized in bioanalytical experiments such as PCR and the like, to isolate aqueous reaction mixtures.

BACKGROUND

Microfluidics has transformed the way traditional procedures in molecular biology, medical diagnostics, and drug discovery are performed. Lab-on-a-chip and biochip type devices have drawn much interest in both scientific research applications as well as potentially for point-of-care applications because they carryout highly repetitive reaction steps with a small reaction volume, saving both materials and time. While traditional biochip-type devices utilize micro- or nano-sized channels and typically require corresponding micropumps, microvalves, and microchannels coupled to the biochip to manipulate the reaction steps, these additional components greatly increase cost and complexity of the microfluidic device.

Digital microfluidics (DMF) has emerged as a powerful preparative technique for a broad range of biological and chemical applications. DMF enables real-time, precise, and highly flexible control over multiple samples and reagents, including solids, liquids, and even harsh chemicals, without need for pumps, valves, or complex arrays of tubing. In DMF, discrete droplets of nanoliter to microliter volumes are dispensed from onto a planar surface coated with a hydrophobic insulator, where they are manipulated (transported, split, merged, mixed) by applying a series of electrical potentials to an embedded array of electrodes. Complex reaction steps can be carried out using DMF alone, or using hybrid systems in which DMF is integrated with channel-based microfluidics.

Despite significant advances, both evaporation, particularly in air-matrix DMF, and surface fouling remain issues. Surface fouling occur when components from the reaction mixture irreversibly adheres to surfaces of the microfluidic or DMF device after contacting these surfaces. Surface fouling is a particularly acute problem when operating a higher (e.g., greater than 37° C.) temperatures. Various strategies have been proposed to prevent surface fouling, such as using polymers, glass, and metals to fabricate the microfluidic channels or chemical modification of material surfaces. However, these strategies have had limited success, particularly in the context of DMF, despite efforts to test and fabricate surfaces and surface coatings that are resistant to surface fouling. In some instances, a coating on surfaces intended to prevent surface fouling may cause undesirable interactions and secondary reactions with the reaction mixture and/or reagents used. In other instances, chemical additives have been proposed for use within the droplets employed within DMF, but are not universally applicable to all experimental conditions, as no one additive is effective for all fouling reagents/reaction components and equally, no one additive is compatible with the range of assay constituents such as enzymes or cells. In general, it would be desirable to have a simple solution to minimizing surface fouling in microfluidic and DMF devices.

Evaporation is also a concern when performing reactions in an air-matrix DMF device. In general, an air-matrix DMF apparatus may refer to any non-liquid interface of the DMF apparatus in which the liquid droplet being manipulated by the DMF apparatus is surrounded by an air (or any other gas) matrix. As used herein, an air-matrix may also and interchangeably be referred to as a "gas-matrix" DMF apparatus; the gas does not have to be air, though it may be. Evaporation may be especially problematic in air-matrix DMF methods and that heat for a prolonged period of time (e.g., greater than 0 seconds). Evaporation limits the utility of air-matrix DMF, because enzymatic reactions are often highly sensitive to changes in reactant concentration. Largely for this reason, others have attempted to use oil-matrix DMF for biochemical applications, despite numerous drawbacks including: the added complexity of incorporating gaskets or fabricated structures to contain the oil; unwanted liquid-liquid extraction of reactants into the surrounding oil; incompatibility with oil-miscible liquids (e.g., organic solvents such as alcohols); and efficient dissipation of heat, which undermines localized heating and often confounds temperature-sensitive reactions. Another strategy for addressing evaporation has been to place the air-matrix DMF device in a closed humidified chamber, but this often results in unwanted condensation on the DMF surface, difficult and/or limited access to the device, and a need for additional laboratory space and infrastructure.

It has also been proposed to address evaporation by transferring reaction droplets from the air-matrix DMF device to microcapillaries, where they can be heated in dedicated off-chip modules without evaporation problems. However, this complicates design and manufacture of the air-matrix DMF device, and introduces the added complications of microcapillary interfaces and coordination with peripheral modules.

Thus, there exists a need for compositions for use in air-matrix DMF apparatuses and methods that may prevent or limit surface fouling in combination with compositions which limit or prevent evaporation. Described herein are apparatuses and methods that may address this need.

SUMMARY OF THE DISCLOSURE

Described herein are mobilizing wax compositions that may be used, e.g., as part of a digital microfluidics (DMF) method or system to both prevent or reduce evaporation of an aqueous droplet and to prevent surface fouling. The mobilizing wax compositions described herein may be particularly helpful in DMF apparatuses having an air gap, for which both surface fouling and evaporation are potentially problematic. The mobilizing wax compositions described herein, by including the anti-fouling agent as part of the mobilizing wax composition instead of within the aqueous droplet itself, may also be advantageous.

A typical DMF apparatus may include parallel surfaces (which may be referred to as 'plates' herein) separated by an air gap; one of the plates (typically the bottom plate) may be in electrical contact with a patterned array of individually controllable actuation electrodes, and the opposite plate (e.g., the top plate) may include and/or be in electrical contact with one or more ground electrode(s). The one or more ground electrode(s) can be provided on the same plate as the actuating (e.g., high-voltage) electrodes. The surfaces of the plates in the air gap may include a hydrophobic material which may be dielectric or in some variations an additional dielectric layer may be included. The hydrophobic and/or dielectric layer(s) may decrease the wettability of the surface and add capacitance between the droplet and the control electrode. Droplets may be moved or otherwise manipulated while in the air gap space between the plates. The air gap may be divided up into regions, and some regions of the plates may include heating/cooling by a thermal regulator (e.g., a Peltier device, a resistive heating device, a convective heating/cooling device, etc.) that is in thermal contact with the region, and may be localized to that region. Reactions performed on with the air-matrix DMF apparatus may be detected, including imaging or other sensor-based detection, and may be performed at one or more localized regions or over all or over a majority of the air gap space of the air-matrix DMF apparatus.

Evaporation is a challenge when using droplets within an air gap, particularly when heating. To prevent or reduce evaporation, an outer sheath of hydrophobic material, such a wax or other material that is liquid in the operational temperature range (e.g., between about 10 degree C. to about 120 degree C., between about 5 degrees C. to about 120 degrees C., between about 1 degrees C. to about 110 degrees C., between about 0 degrees C. to about 100 degrees C., between about −5 degrees C. to about 120 degrees C., or any range within these, including a lower temperature of −10, −5, −1, 0, 1, 2, 3, 4, 5, 10, 12, 15, etc. degrees C. and an upper temperature of 100, 101, 105, 110, 120, 130, etc. degrees C.), referred to herein as a liquid wax. Even with the use of a liquid wax to encapsulate a droplet in an air gap to prevent evaporation, in some cases it may be difficult to prevent surface fouling during extended reaction periods or upon incorporating materials that are susceptible to fouling. Thus, moving wax encapsulated droplets within the air gap may become increasingly difficult, including moving to a reaction region (e.g., having temperature control). A droplet may become immobile during or upon completion of a reaction protocol.

Thus, described herein are compositions, methods and kits for performing one or more droplet operations (including merging with additional aqueous droplets) using a mobilizing wax composition to coat, cover, encapsulate, sheath, etc. an aqueous droplet, which may both prevent or reduce evaporation and prevent or eliminate fouling without requiring the addition of an anti-fouling agent to mix in the aqueous droplet itself. Instead a generally lipophilic agent (e.g., an agent having a hydrophilic-lipophilic balance, HLB, of about 10 or less, e.g., about 9 or less, about 8 or less, about 7 or less, about 6 or less, etc.) may be added into the liquid wax material coating the droplet to form the mobilizing wax. The composition including the liquid wax and the generally lipophilic agent may be referred to herein as a mobilizing wax composition. In any of the composition and methods described herein, the composition (and any droplet used with the composition) does not include a hydrophilic polymer additive (e.g., a nonionic surfactant).

Any of the methods described herein may be referred to as a method of performing droplet operations on a droplet that is at least partially coated in a mobilizing wax composition within an air-matrix digital microfluidic (DMF) apparatus (e.g., within the air gap of the air-matrix DMF apparatus). In general, these methods may include starting with the aqueous droplet (e.g., adding it into the air gap of the DMF apparatus), and using electrowetting to move it within the air gap. The methods may also generally include encapsulating with a mobilizing wax composition as described in more detail. This may be used to perform any procedure within the air gap, including a thermally-regulated procedure. Further, any of these methods may also typically include removing much or most of the mobilizing wax composition from the aqueous droplet, e.g., by suction, by using a lipophilic wicking agent, and/or by moving the droplet away, e.g., by electrowetting, etc.).

In addition, any of these methods may generally include: moving, by electrowetting, an aqueous reaction droplet having an outer coating of the mobilizing wax composition (which may be just a very thin layer at least partially coating the aqueous droplet) within an air gap of the air-matrix DMF apparatus (as expected, the air gap may be formed between a first plate and a second plate of the air-matrix DMF apparatus). Any of these methods may also include merging, in the air gap, the aqueous reaction droplet with additional droplets, such as with a carrier droplet comprising an aqueous droplet that may be uncoated or may also be coated, e.g., with a liquid wax as described herein and/or another oil or an organic solvent (with our without the generally lipophilic anti-fouling agent) to form a combined droplet. The oil or organic solvent may be coated in a thin (e.g., monolayer or thicker) layer on the second aqueous droplet but interact with the mobilizing wax coating on the first aqueous droplet and permit the two to merge; in the absence of this oil or organic solvent, the two droplets will not merge. Thereafter, the methods may include moving, by electrowetting, the combined droplet within the air gap. The second aqueous droplet may include any material (buffer, marker, beads, wash, etc.). This process may be repeated multiple times, e.g., by combining the combined droplet with additional aqueous droplets including an oil or organic solvent.

In some variations, the mobilizing wax, oil or organic solvent material may be separated from the combined droplet or target molecules in the combined droplet. For example, beads (e.g., magnetic beads) holding the target molecule(s) may be separated magnetically from the combined droplet, including the outer coating (e.g., mobilizing wax and oil/organic solvent). The beads may then be washed to remove any residual coating. Alternatively, in some variations, the coating may be mechanically removed (e.g., by wicking).

Also described herein are methods of preventing droplet evaporation within an air-matrix digital microfluidic (DMF) apparatus, the method may include: introducing a reaction droplet into an air gap of the air-matrix DMF apparatus which is formed between a first plate and a second plate of the air-matrix DMF apparatus; combining the aqueous reaction droplet with a mobilizing wax material to sheath the droplet within the air gap of the air-matrix DMF (alternatively in any of these methods the mobilizing wax may be combined with the aqueous droplet prior to or concurrent with placement of the droplet into the air gap); moving or otherwise performing operations on the reaction droplet with the mobilizing wax while the mobilizing wax protects the reaction droplet from evaporation and allows a reaction to proceed within the reaction droplet.

Introducing the reaction droplet into an air gap may comprise combing multiple droplets to form a reaction droplet within the air gap; all or some of these may include a mobilizing wax sheath. The first plate may be in electrical contact with a plurality of adjacent actuation electrodes, and wherein combining the reaction droplet with the mobilizing wax comprises applying energy to a subset of the actuation electrodes of the plurality of adjacent actuation electrodes to move the reaction droplet and mobilizing wax sheath.

As mentioned, the methods and compositions described herein may be used with an air gap formed between a first plate and a second plate; the plates may be formed of any appropriate material. In some variations the air gap is part of a cartridge that includes a dielectric sheet forming the bottom plate; the cartridge may be inserted into a device including an array of drive electrodes that may be placed in electrical communication with the air gap through the dielectric. Alternatively, in some variations, the first plate may comprise a plurality of adjacent actuation (drive) electrodes. Combining the reaction droplet with the mobilizing wax composition may comprise applying energy to a subset of the actuation electrodes of the plurality of adjacent actuation electrodes to move the reaction droplet in contact with the mobilizing wax composition.

In some variations, allowing a reaction to proceed may comprise controlling the temperature of a droplet; e.g., cooling and/or heating at least a portion of the air gap containing the reaction droplet. As mentioned, any of these methods may include detecting a product within the reaction droplet.

Accordingly, in a first aspect, a composition for preventing surface fouling is provided which includes a mobilizing wax composition. The mobilizing wax composition may include a wax component for encapsulating an aqueous droplet and a lipophilic mobilizing component for preventing surface fouling. Use of this composition to at least partially, substantially or entirely encapsulate an aqueous droplet may mobilize the aqueous droplet. The encapsulation may also prevent or reduce evaporation from the droplet.

The wax component may be a liquid wax at temperatures from about 0° C. to about 120° C.; about 4° C. to about 100° C.; about 7° C. to about 100° C.; about 10° C. to about 100° C., or about 20° C. to about 100° C. In some other embodiments, the wax component may be a liquid wax at temperatures from about 4° C. to about 100° C., about 7° C. to about 100° C. or about 10° C. to about 100° C.

In various embodiments of the composition, the liquid wax of the wax component may include one or more non-polar compounds comprising hydrocarbon oils, silicone oils, fluorinated oils, plant-based oils, or any combination thereof. In some embodiments, the liquid wax may be liquid paraffin oil, mineral oil or a linear hydrocarbon molecule having more than 10 backbone carbons. Thus, the term "wax" and "wax" components described herein are not limited to paraffins, but may include plant waxes, animal waxes, petroleum derived waxes, etc. In yet other embodiments, the liquid wax may be liquid paraffin oil or mineral oil. In some further embodiments, the liquid wax may be liquid paraffin oil.

In various embodiments of the composition, the liquid wax may be selected to include only those that have a density from about 0.75 g/ml to about 0.90 g/ml at 20° C. In some embodiments, the liquid wax may have a density of about 0.77 g/ml. In various embodiments of the composition, the liquid wax may be selected to include only those that have a contact angle from about 20 to about 65 degrees. In some embodiments, the liquid wax may have a contact angle of about 30 to about 35 degrees.

In various embodiments of the composition, the lipophilic mobilizing component of the mobilizing wax composition may include a molecule having a hydrophilic-lipophilic balance (HLB) less than about 10 (e.g., less than about 9, less than about 8, less than about 7, etc.). In some embodiments, the lipophilic mobilizing component may be a non-ionic surfactant. Such agents may be referred to herein as a generally lipophilic agent.

In some embodiments, the lipophilic mobilizing component may be one or more of: Brij® 93 (e.g., polyethylene glycol oleyl ether), Span® 20 (sorbitan laurate), Span® 40 (sorbitan monopalmitate), Span® 60 (sorbitan stearate), Span® 65 (sorbitan tristearate), Span® 80 (sorbitan oleate), Span® 85 (sorbitane trioleate), 1-Stearoyl-rac-glycerol, phosphatidylcholine (lecithin), Sorbitan sesquioleate, Tetronic® 90R4 (ethylenediamine tetrakis(ethoxylate-block-propoxylate) tetrol), Tetronic® 701 (ethylenediamine tetrakis(propoxylate-block-ethoxylate) tetrol), Pluronic® L-31, Pluronic® L-61, Pluronic® L-81, Pluronic® L-121, Pluronic® 31R1, Brij® 52 (polyethylene glycol hexadecyl ether), MERPOL® A, or any combination thereof. In some embodiments, the lipophilic mobilizing component may be Brij® 93.

In various embodiments of the composition, the lipophilic mobilizing component may be present in a concentration (v/v %) from about 0.001% to about 10%; about 0.001% to about 1.0%; about 0.001% to about 0.10%; about 0.01% to about 10%; about 0.01% to about 1.0%; about 0.01% to about 0.10%, or any value there between. In some embodiments, the lipophilic mobilizing component may be present in a concentration (v/v %) from about 0.01% to about 0.10%.

In various embodiments of the composition the aqueous droplet that is encapsulated by the mobilizing wax compositions may contain a biological sample of interest, reagent, a micro-object, or any combination thereof. In some embodiments, the micro-object may be one or more beads, one or more biological cells, one or more subcellular portions of a cell, or any combination thereof.

A method of preventing surface fouling within an air-matrix digital microfluidic (DMF) apparatus is provided, where the method includes: moving, by DMF, an aqueous droplet into an air gap of the air-matrix DMF apparatus which is formed between a first plate and a second plate of the air-matrix DMF apparatus wherein the droplet is encapsulated aqueous droplet within a sheath of a mobilizing wax composition comprising a liquid wax and a lipophilic mobilizing component for preventing surface fouling. The encapsulated sheath of mobilizing wax may be any thickness or size (e.g., equal to a volume that is between 300% and 30% the volume of the aqueous droplet, between about 250% and 40% the volume of the aqueous droplet, between about 200% and 50% the volume of the aqueous droplet, etc.).

In another aspect, a method of preventing surface fouling within an air-matrix digital microfluidic (DMF) apparatus is provided, where the method includes: introducing an aqueous droplet into an air gap of the air-matrix DMF apparatus which is formed between a first plate and a second plate of the air-matrix DMF apparatus; and encapsulating the aqueous droplet within a sheath of a mobilizing wax composition comprising a liquid wax and a lipophilic mobilizing component for preventing surface fouling.

In various embodiments of the method of preventing surface fouling, the mobilizing wax composition may be any mobilizing wax composition described herein. In some embodiments, the liquid wax component may be liquid paraffin and the lipophilic mobilizing component may be Brij® 93 (e.g., Polyethylene glycol oleyl ether).

In various embodiments, introducing the aqueous droplet into an air gap may include combining multiple droplets to form the aqueous droplet within the air gap.

In various embodiments, the mobilizing wax composition may be introduced in a mixture with the aqueous drop while introducing the aqueous drop into the air-gap. In other embodiments, the first plate may include a plurality of adjacent actuation electrodes, and wherein encapsulating the aqueous droplet with the mobilizing wax composition may further include transporting the aqueous droplet to a droplet preparation zone of the air gap, wherein the droplet preparation zone includes the mobilizing wax composition. In some embodiments, the first plate may include a plurality of adjacent actuation electrodes, and combining the aqueous droplet with the mobilizing wax composition may include applying energy to a subset of the actuation electrodes of the plurality of adjacent actuation electrodes thereby moving the aqueous droplet into contact with the mobilizing wax composition.

In some embodiments of the method, the aqueous droplet may include a reagent, a micro-object or a combination thereof. In various embodiment, the micro-object may be a bead, a biological cell, a subcellular portion of a cell, or any combination thereof.

In yet another aspect, a method of performing droplet operations on a droplet at least partially coated in a mobilizing wax composition within an air-matrix digital microfluidic (DMF) apparatus is provided, the method including: a first aqueous droplet having an outer coating of a mobilizing wax composition within an air gap of the air-matrix DMF apparatus which is formed between a first plate and a second plate of the air-matrix DMF apparatus, wherein the mobilizing wax composition comprises a liquid wax and a lipophilic mobilizing component for preventing surface fouling.

In various embodiments of the method of performing droplet operations, the mobilizing wax composition may be any mobilizing wax composition as described herein. In some embodiments, the first aqueous droplet may be a reaction droplet.

In various embodiments, wherein moving, by electrowetting, the first aqueous droplet may include initially transporting the first aqueous droplet to a droplet preparation zone of the air gap, the droplet preparation zone comprising the mobilizing wax composition and at least partially encapsulating the first aqueous droplet with the mobilizing wax composition. In some embodiments, wherein moving, by electrowetting, the at least partially encapsulated first aqueous droplet comprises transferring the at least partially encapsulated first aqueous droplet away from away from the droplet preparation zone so that at least some of the mobilizing wax composition is left behind.

In various embodiments of the method, the method may further include merging the at least partially encapsulated first aqueous droplet with a carrier droplet comprising a second aqueous droplet coated with an oil or an organic solvent in the air gap to form an at least partially encapsulated combined aqueous droplet. The carrier droplet may include beads, a reagent, a primer, a dilution buffer, an enzyme, a protein, a nanopore, a wash buffer, an alcohol, formamide, a detergent, or any suitable combination thereof.

In various embodiments of the method, the method may further include moving the at least partially encapsulated first aqueous droplet or combined aqueous droplet, by electrowetting, to a thermal zone of the air gap; and regulating the temperature of the at least partially encapsulated first aqueous droplet or combined aqueous droplet to allow a reaction to proceed within the respective droplet before transporting the at least partially encapsulated first aqueous droplet or combined aqueous droplet within the air gap.

In various embodiments of the method, the method may further include detecting a product within the at least partially encapsulated aqueous droplet or combined aqueous droplet.

In various embodiments of the method, merging the at least partially encapsulated first aqueous droplet with the carrier droplet may include moving one or both of the at least partially encapsulated first aqueous droplet and the carrier droplet into contact with each other by electrowetting.

In various embodiments of the method, when the at least partially encapsulated first aqueous droplet or the combined aqueous droplet includes a plurality of beads, the method may further include mixing the respective droplet. In some embodiments, the method may further include immobilizing the beads. In some other embodiments, the method may further include moving the at least partially encapsulated combined aqueous droplet or the combined aqueous droplet away from the immobilized beads. In yet other embodiments, the method may further include re-suspending the immobilized beads within a reaction product aqueous droplet. In further embodiments, the method may further include separating the beads from the at least partially encapsulated combined aqueous droplet by moving a magnetic field away from the combined droplet to magnetically draw the beads away from the combined droplet.

In another aspect, a method of performing a reaction within an air-matrix digital microfluidic (DMF) apparatus is provided, the method including: introducing an aqueous reaction droplet into an air gap of the air-matrix DMF apparatus which is formed between a first plate and a second plate of the air-matrix DMF apparatus, wherein the aqueous reaction droplet is at least partially encapsulated with a mobilizing wax composition comprising a liquid wax and a lipophilic mobilizing component for preventing surface fouling; regulating the temperature of the at least partially encapsulated aqueous reaction droplet to allow a reaction to proceed within the at least partially encapsulated aqueous reaction droplet; and transporting the at least partially encapsulated aqueous reaction droplet away from the thermal zone after the reaction is completed. In various embodiments, the mobilizing wax composition may be any mobilizing wax composition as described herein.

In various embodiments of the method of performing a reaction, introducing the aqueous reaction droplet into an air gap may include combining multiple droplets to form the aqueous reaction droplet within the air gap. In some embodiments, introducing the aqueous reaction droplet into the air gap further may include introducing the aqueous droplet in a mixture with the mobilizing wax composition into the air gap. In other embodiments, introducing the aqueous reaction droplet into the air gap further may include encapsulating the aqueous reaction droplet with a mobilizing wax composition thereby producing an at least partially encapsulated aqueous reaction droplet. In some embodiments, encapsulating the aqueous reaction droplet may further include initially transporting the first aqueous droplet to a droplet preparation zone of the air gap, the droplet preparation zone comprising the mobilizing wax composition and at least partially encapsulating the first aqueous droplet with the mobilizing wax composition. In some embodiments, the first plate includes a plurality of adjacent actuation electrodes, and wherein at least partially encapsulating the aqueous reaction droplet with the mobilizing wax composition may include applying energy to a subset of the actuation electrodes of the plurality of adjacent actuation electrodes to move the aqueous reaction droplet in contact with the mobilizing wax composition.

In various embodiments of the method of performing a reaction, the method may further include detecting a product within the at least partially encapsulated aqueous reaction droplet after completing the reaction.

In various embodiments of the method, the at least partially encapsulated aqueous reaction droplet may further include beads, and the method may further include mixing the reaction droplet. In various embodiments of the method, the method may further include immobilizing the beads. In other embodiments of the method, the method may further include moving the at least partially encapsulated aqueous reaction droplet away from the immobilized beads. In yet other embodiments of the method, the method may further include re-suspending the immobilized beads with a reaction product aqueous droplet. In further embodiments of the method, the method may further include separating the beads from the at least partially encapsulated combined droplet by moving a magnet away from the at least partially encapsulated combined droplet.

In various embodiments of the method, introducing the aqueous reaction droplet in to the air gap may further include merging the at least partially encapsulated aqueous reaction droplet with a carrier droplet comprising an aqueous droplet coated with an oil or an organic solvent in the air gap thereby forming an at least partially encapsulated combined droplet; regulating the temperature of the at least partially encapsulated aqueous reaction droplet to allow a reaction may further include regulating the temperature of the at least partially encapsulated combined droplet to allow a reaction to proceed within the at least partially encapsulated aqueous reaction droplet; and transporting the at least partially encapsulated aqueous reaction droplet away from the thermal zone after the reaction is completed may further include transporting the at least partially encapsulated combined droplet away from the thermal zone after the reaction is completed.

In various embodiments of the method, the carrier droplet may include beads, a reagent, a primer, a dilution buffer, an enzyme, a protein, a nanopore, a wash buffer, an alcohol, formamide, a detergent, or any suitable combination thereof. In some embodiments, when the carrier droplet comprises beads, the method may further include mixing the reaction droplet. In some embodiments, the method may further include immobilizing the beads. In some embodiments, the method may further include moving the at least partially encapsulated combined droplet away from the immobilized beads. In some embodiments, the method may further include re-suspending the immobilized beads with a reaction product aqueous droplet. In some embodiments, the method may further include separating the beads from the at least partially encapsulated combined droplet by moving a magnet away from the at least partially encapsulated combined droplet.

In another aspect, a kit for mobilizing droplets comprising a mobilizing wax composition and a carrier coating formulation. The mobilizing wax composition may be any mobilizing wax composition as described herein. In some embodiments, components of the mobilizing wax composition may be provided in one or more separate containers. In various embodiments of the kit, the carrier coating formulation may be an oil or a lipophilic organic solvent.

In various embodiments of the kit, the kit may further include beads. In some embodiments, the beads may be magnetic. In some embodiments, the beads may be configured to bind to a molecule selected from the group consisting of DNA, RNA, and proteins.

In various embodiments of the kit, the kit may further include a reagent, a primer, a dilution buffer, an enzyme, a protein, a nanopore, a wash buffer, an alcohol, formamide, a detergent, or any suitable combination thereof.

Although the majority of the devices described herein are air-matrix DMF apparatuses that include two parallel plates forming the air gap, any of the compositions and/or methods may be adapted for operation as part of a one-plate air-matrix DMF apparatus. In this case, the apparatus includes a single plate and may be open to the air above the single (e.g., first) plate; the "air gap" may correspond to the region above the plate in which one or more droplet may travel while on the single plate. The ground electrode(s) may be positioned adjacent to (e.g., next to) each actuation electrode, e.g., in, on, or below the single plate. The plate may be coated with the hydrophobic layer (and an additional dielectric layer maybe positioned between the hydrophobic layer and the dielectric layer, or the same layer may be both dielectric and hydrophobic). The compositions and methods for correcting for surface fouling in combination with preventing evaporation may be particularly well suited for such single-plate air-matrix DMF apparatuses.

Although the majority of the devices described herein are air-matrix DMF apparatuses that include two parallel plates forming the air gap, any of the compositions and/or methods may be adapted for operation as part of a one-plate air-matrix DMF apparatus. In this case, the apparatus includes a single plate and may be open to the air above the single (e.g., first) plate; the "air gap" may correspond to the region above the plate in which one or more droplet may travel while on the single plate. The ground electrode(s) may be positioned adjacent to (e.g., next to) each actuation electrode, e.g., in, on, or below the single plate. The plate may be coated with the hydrophobic layer (and an additional dielectric layer maybe positioned between the hydrophobic layer and the dielectric layer, or the same layer may be both dielectric and hydrophobic). The compositions and methods for correcting for surface fouling in combination with preventing evaporation may be particularly well suited for such single-plate air-matrix DMF apparatuses.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 2A-2C are top views of three exemplary droplets upon the surface of an air-matrix DMF apparatus demonstrating portability after exemplary manipulations according to some embodiments of the disclosure.

FIGS. 4A-4C are top views of an exemplary droplet upon the surface of an air-matrix DMF apparatus demonstrating portability after exemplary manipulations according to some embodiments of the disclosure.

DETAILED DESCRIPTION

Figures 1A, 1B:
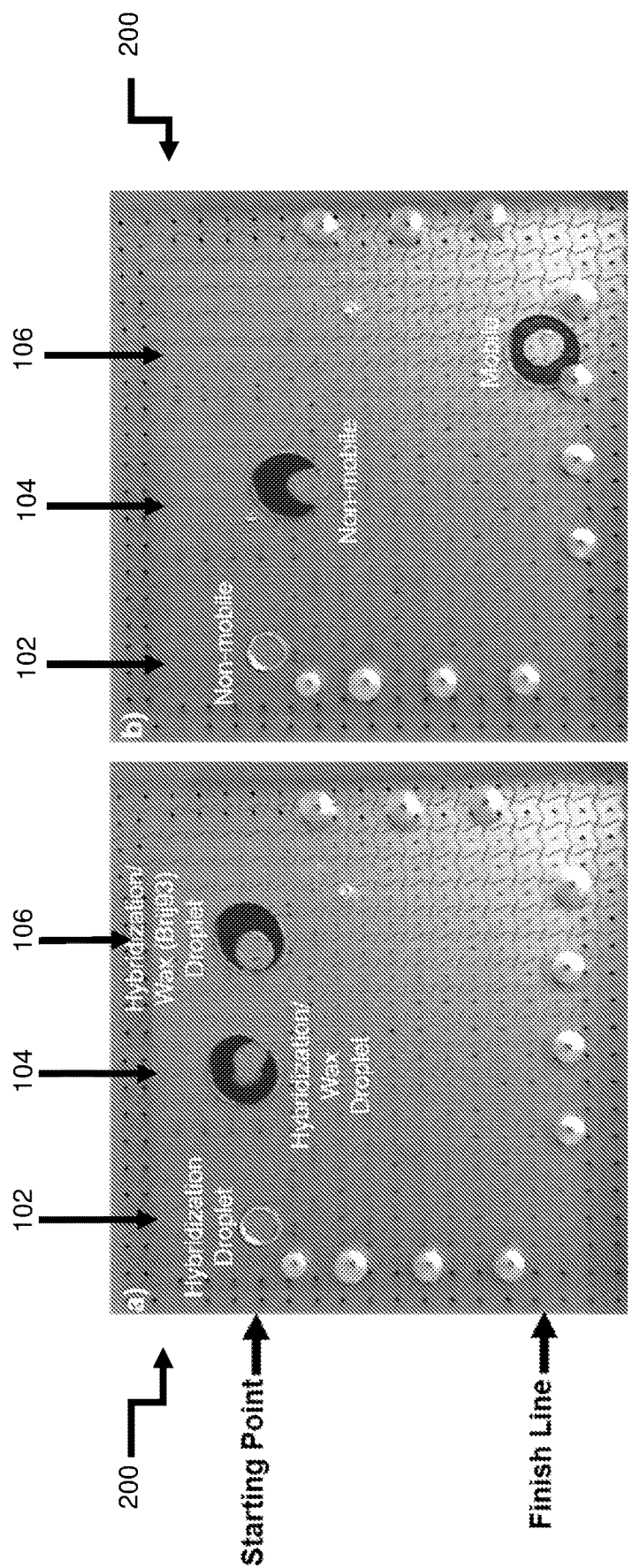
FIGS. 1A-1B are top views of an example of an air-matrix DMF apparatus showing a plurality of unit cells (defined by the underlying actuating electrodes), and including three exemplary droplets demonstrating portability within the DMF apparatus according to some embodiments of the disclosure.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

Described herein are air-matrix digital microfluidics (DMF) methods and apparatuses that may minimize the effect of surface fouling and/or evaporation. An air-matrix DMF apparatus as described herein may be particularly useful when heating the reaction droplets being processed.

In general, an air-matrix DMF apparatus as disclosed herein may have any appropriate shape or size. As used herein, the term "surface fouling" may refer to accumulation of unwanted materials on solid surfaces, including with the air gap of the air matrix DMF apparatus (e.g., upper and/or lower plate surfaces). Surface fouling materials can consist of either living organisms (biofouling) or a non-living substance (inorganic or organic). Surface fouling is usually distinguished from other surface-growth phenomena in that it occurs on a surface of a component, or system and that the fouling process impedes or interferes with function.

The air-matrix DMF apparatuses described herein generally includes at least one hydrophobic surface and a plurality of activation electrodes adjacent to the surface; either the hydrophobic surface may also be a dielectric material or an additional dielectric material/layer may be positioned between the actuation electrodes and the hydrophobic surface. For example, in some variations, the air-matrix DMF includes a series of layers on a printed circuit board (PCB) forming a first or bottom plate. The outer (top) surface of this plate is the hydrophobic layer. Above this layer is the air gap (air gap region) along which a reaction droplet may be manipulated. In some variations a second plate may be positioned opposite from the first plate, forming the air gap region between the two. The second plate may also include a hydrophobic coating and in some variations may also include a ground electrode or multiple ground electrodes opposite the actuation electrodes. The actuation electrodes may be configured for moving droplets from one region to another within the DMF device, and may be electrically coupled to a controller (e.g., control circuitry) for applying energy to drive movement of the droplets in the air gap. As mentioned, this plate may also include a dielectric layer for increasing the capacitance between the reaction droplet and the actuation electrodes. The reaction starting materials and reagents, as well as additional additive reagents may be in reservoirs that may be dispensed into the air gap, where the reaction mixture is typically held during the reaction. In some instances the starting materials, reagents, and components needed in subsequent steps may be stored in separate areas of the air gap layer such that their proximity from each other prevents them from prematurely mixing with each other. In other instances, the air gap layer may include features that are able to compartmentalize different reaction mixtures such that they may be close in proximity to each other but separated by a physical barrier. In general, the floor of the air gap is in the first plate, and is in electrical contact with a series of actuation electrodes.

The air gap DMF apparatuses described herein may also include other elements for providing the needed reaction conditions. For instance, the air gap DMF apparatuses may include one or more thermal regulators (e.g., heating or cooling element such as thermoelectric modules) for heating and cooling all or a region (thermal zone) of the air gap. In other instances, heating or cooling may be provided by controlling endothermic or exothermic reactions to regulate temperature. The air gap DMF apparatuses may also include temperature detectors (e.g., resistive temperature detector) for monitoring the temperature during a reaction run. In addition, the DMF apparatuses may also include one or more magnets that can be used to manipulate magnetic beads in an on demand fashion. For example, the magnet(s) can be an electromagnet that is controlled by a controller to generate a magnetic field that can agitate or immobilize magnetic beads.

Thus, the air gap DMF apparatuses described herein may include one or more thermal zones. Thermal zones are regions on the air gap DMF apparatuses (e.g., the air gap) that may be heated or cooled, where the thermal zones may transfer the heating or cooling to a droplet within the thermal zone through one or more surfaces in contact with the air gap region in the zone (e.g., the first plate). Heating and cooling may be through a thermal regulator such as a thermoelectric module or other type of temperature-modulating component. The temperature of one or many thermal zones may be monitored through a temperature detector or sensor, where the temperature information may be communicated to a computer or other telecommunication device. The temperature is typically regulated between 4° C. and 100° C., as when these apparatuses are configured to perform one or more reactions such as, but not limited to: nucleic acid amplifications, like LAMP, PCR, molecular assays, cDNA synthesis, organic synthesis, etc.

An air gap DMF apparatus may also include one or more thermal voids. Thermal voids may be disposed adjacent to the different thermal zones. The thermal voids are typically regions in which heat conduction is limited, e.g., by removing part of the plate (e.g., first plate) (forming the "void"). These voids may be strategically placed to isolate one thermal zone from another which allows the correct temperatures to be maintained within each thermal zone.

Figure 6:
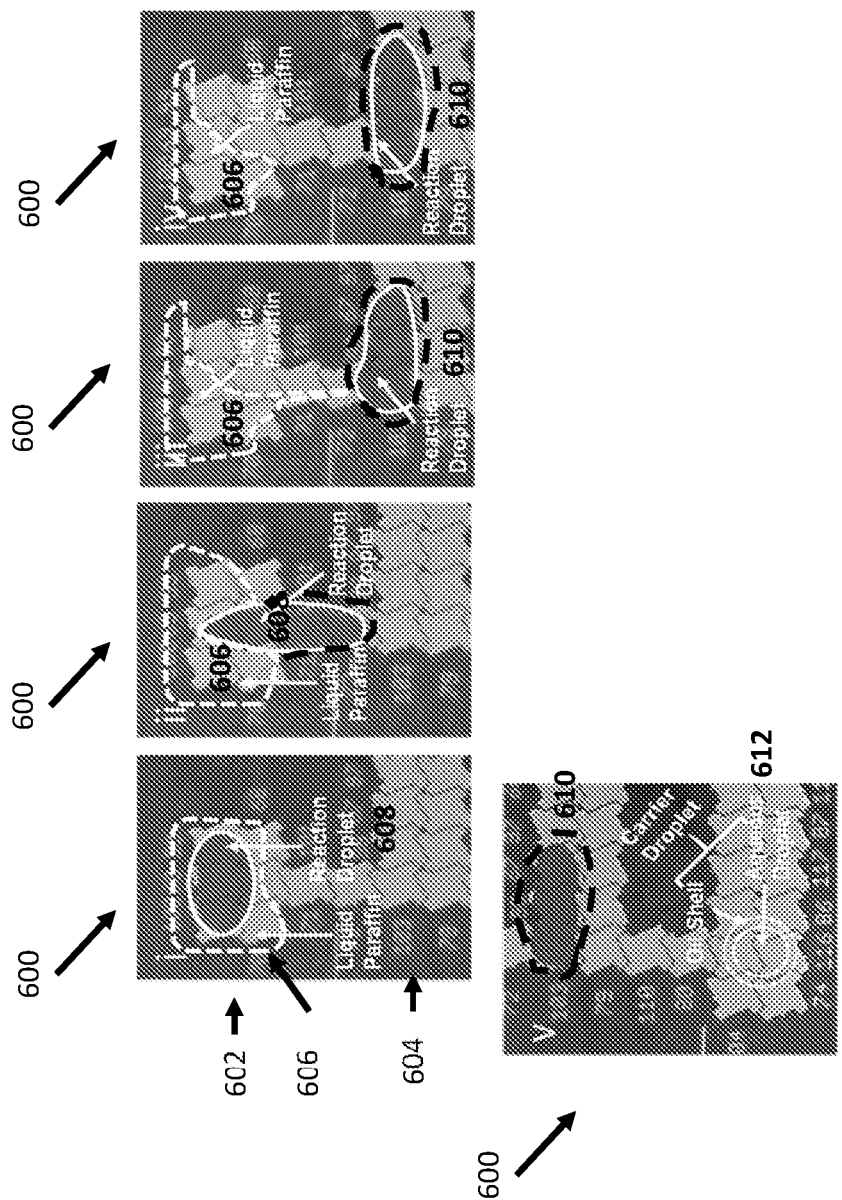
FIG. 6 includes top views of the process of encapsulating a reaction droplet upon the surface of an air-matrix DMF apparatus according to some embodiments of the disclosure.

FIG. 6 shows a top view of a portion of an exemplary air-matrix DMF apparatus 600. As shown, the DMF device may include a series of paths defined by actuation electrodes. The individual actuation electrodes of the electrode array 604 are shown in FIG. 6 as a series of polygons, each defining a unit cell. These actuation electrodes may have any appropriate shape and size, and are not limited to squares. For example, the unit cells formed by the actuation electrodes in the first layer may be round, hexagonal, triangular, rectangular, octagonal, parallelogram-shaped, etc. In the example of FIG. 6, the squares representing the unit cells may indicate the physical location of the actuation electrodes in the DMF device or may indicate the area where the actuation electrode has an effect (e.g., an effective area such that when a droplet is situated over the denoted area, the corresponding actuation electrode may affect the droplet's movement or other physical property). The actuation electrodes may be placed in any pattern. In some examples, actuation electrodes may span the entire corresponding bottom or top surface the air gap of the DMF apparatus. The actuation electrodes may be in electrical contact with starting sample chambers (not shown) as well as reagent chambers (not shown) for moving different droplets to different regions within the air gap to be mixed with reagent droplets or heated.

In general, one or more additional reagents may be subsequently introduced either manually or by automated means in the air gap. In some instances, access holes to the air gap may be actual access ports that may couple to outside reservoirs of reagents or reaction components through tubing for introducing additional reaction components or reagents at a later time. As mentioned, the access holes) may be located in close proximity to a DMF actuation electrode (s). Access holes may also be disposed on the side or the bottom of the DMF apparatus. In general, the apparatus may include a controller for controlling operation of the actuation electrodes, including moving droplets into and/or out of reaction chambers. The controller may be in electrical communication with the electrodes and it may apply power in a controlled manner to coordinate movement of droplets within the air gap and into/out of the reaction chambers. The controller may also be electrically connected to the one or more temperature regulators (thermal regulators) to regulate temperature in the thermal zones. One or more sensors (e.g., video sensors, electrical sensors, temperature sensors, etc.) may also be included (not shown) and may provide input to the controller which may use the input from these one or more sensors to control motion and temperature.

Despite the ease of use for performing droplet manipulations and reactions in an air-matrix DMF apparatus, evaporation is a long-standing problem when using DMF apparatuses and may affect drop manipulation as well as sample preparation/assay protocols. If evaporation is not prevented during the course of a protocol, it may result in concentrating the reaction mixture. This concentration may be detrimental as reagents may be volatilized or drop out of solution, altering the concentration of the reaction mixture and resulting in mismatched concentration between the intermediate reaction droplet with subsequent addition of other reaction materials of a given concentration. In some variations, such as with enzymatic reactions, enzymes are highly sensitive to changes in reaction environment and loss of reagent may alter the effectiveness of certain enzymes. Evaporation is especially problematic when the reaction mixture has to be heated to above ambient temperature for an extended period of time.

Additionally, surface fouling is another important issue that has plagued microfluidics, including DMF devices. Surface fouling occurs when certain constituents of a reaction mixture irreversibly adsorbs onto a surface that the reaction mixture is in contact with. Surface fouling also appears more prevalent in samples containing proteins and other biological molecules. Increases in temperature may also contribute to surface fouling. Fouling can result in contamination of a droplet and can lead to the inability to move the droplet from the location where the fouling was contacted or produced.

The recent applications of DMF devices for increasingly complex processes such DNA library preparation for NGS sequencing analysis as well as multistep DNA assembly workflows for synthetic biology and downstream cell culture assays (which necessitate the long-term actuation of solutions containing high concentrations of proteins and incubations at elevated, cycling temperatures) have required a better solution for biofouling, which can work in tandem with materials that simply act to prevent evaporation.

Applicant has discovered compositions and methods that minimize the effects of surface fouling while also providing protection to a droplet from evaporation, by encapsulating a droplet within a mobilizing wax composition containing a wax component for encapsulating an aqueous droplet and a lipophilic mobilizing component which, added to the composition encapsulating the droplet, minimizes the effect of surface fouling. An additional benefit is provided to insulate the encapsulated droplet form other potentially interfering substances present within the apparatus housing the droplet. While this composition may be used beneficially within an air-matrix DMF apparatus, minimization of evaporation, surface fouling and external-to-droplet interfering substances may also be afforded when these compositions are used in typical laboratory reaction vessels for hybridization, PCR and the like.

Mobilizing wax composition. A composition for preventing surface fouling and evaporation comprising a mobilizing wax composition is described herein, wherein the mobilizing wax composition includes a wax component for encapsulating an aqueous droplet; and a lipophilic mobilizing component for preventing surface fouling, thereby mobilizing the aqueous droplet. Through this approach of enclosing a droplet in a shell of liquid wax including the lipophilic mobilizing components, the reaction volume and temperature are maintained constant without the use of an oil-matrix, a humidified chamber, off-chip heating, or droplet replenishment methods. Further, the lipophilic mobilizing component ensures that the encapsulated aqueous droplet remains mobile within the air-matrix DMF apparatus. A thin layer of the liquid wax infused with low concentration of lipophilic molecules substantially prevents or remediates the surface fouling tendencies for droplets containing problematic materials. This mobilizing wax composition also substantially prevents or remediates surface fouling for droplets subjected to long reaction periods, particularly reactions using elevated temperatures within all or part of the reaction period. Without being bound by theory, the observed effects on non-surface fouling by the compositions described herein, may be a result of layers of lipophilic polymers (for a lipophilic mobilizing component like Brij® 93 (e.g., Polyethylene glycol oleyl ether), but not so limited, The layers of lipophilic polymer may congregate at the low energy surfaces of water-liquid wax interface, wherein a hydrophilic head group of the lipophilic polymer is oriented toward water, and the hydrophobic tail is oriented toward the liquid wax). These layers in droplets manipulated by digital microfluidics could prevent adsorption of proteins and other constituents.

Wax component. In the mobilizing wax compositions described herein, the wax component may be a liquid wax. In some embodiments, the liquid wax may remain liquid at temperatures from about 0° C. to about 120° C. In other embodiments, the liquid wax remains liquid at temperatures from about 4° C. to about 100° C. In yet other embodiments, the liquid wax remains liquid at temperatures from about 7° C. to about 100° C. In some other embodiments, the liquid wax remains liquid at temperatures from about 10° C. to about 100° C. In further embodiments, the liquid wax remains liquid at temperatures from about 20° C. to about 100° C.

The liquid wax, which may be an oil, includes one or more non-polar compounds comprising hydrocarbon oils, silicone oils, fluorinated oils, plant-based oils, or any combination thereof. Hydrocarbon oils include mineral oils, paraffin oils (e.g., Undecane, Dodecane, Tridecane, Tetradecane, Pentadecane, Hexadecane, Heptadecane, Octadecane, Nonadecane, Eicosane), e.g., hydrocarbon molecules typically having more than ten carbon backbone atoms. Hydrocarbon oils may be one or more saturated hydrocarbons or may include one or more sites of unsaturation. Silicone oils, including but not limited to polydimethylsiloxane, may be used within the liquid wax component. In other embodiments, a fluorinated oil, including Fluorinert™, available from 3M may be used within the liquid wax component. Plant based oils include vegetable oils, seed oils and/or nut oils. In some embodiments, a plant based oil such as jojoba oil (Sigma-Aldrich Catalog No. W530293) may be used within the liquid wax component of the mobilizing wax composition.

In particular, the liquid wax described herein may be, for example, hexadecane. The liquid wax may be pure (e.g., 95% pure or more, 96% pure or more, 97% pure or more, 98% pure or more, 99% pure or more, etc.).

For the liquid wax component of the mobilizing wax composition, the liquid wax may have a density from about 0.75 g/ml to about 0.90 g/ml at 20° C. In some embodiments, the liquid wax component may have a density of about 0.75 g/ml, 0.76 g/ml, 0.77 g/ml, 0.78 g/ml, 0.79 g/ml, 0.80 g/ml, 0.81 g/ml, 0.82 g/ml, 0.83 g/ml, 0.84 g/ml, 0.85 g/ml, 0.86 g/ml, 0.87 g/ml, 0.88 g/ml, 0.89 g/ml, or about 0.90 g/ml.

For the liquid wax component of the mobilizing wax composition, the liquid wax may have a contact angle from about 20 to about 65 degrees with a solid surface. The contact angle may be measured using static sessile goniometry. In some embodiments, the liquid wax component may have a contact angle of about 20, 25, 30, 35, 40, 45, 45, 50, 55, 60, 65 degrees, or any value in between these values recited here. For example, liquid paraffin has a contact angle of about 30 degrees.

In some embodiments, a wax component of the mobilizing wax composition may be liquid paraffin, mineral oil or jojoba oil. For example, the liquid wax component may be hexadecane.

Lipophilic mobilizing component. In the mobilizing wax compositions described herein, the lipophilic mobilizing component may include a molecule having a hydrophilic-lipophilic balance (HLB) less than 7. In some embodiments, the lipophilic mobilizing component may be a non-ionic surfactant. In various embodiments, the lipophilic mobilizing component may be, e.g., Brij® 93, Span® 20, Span® 40, Span® 60, Span® 65, Span® 80, Span® 85, 1-Stearoyl-rac-glycerol, phosphatidylcholine (lecithin), Sorbitan sesquioleate, Tetronic® 90R4, Tetronic® 701, Pluronic® L-31, Pluronic® L-61, Pluronic® L-81, Pluronic® L-121, Pluronic® 31R1, Brij® 52, and MERPOL® A or any combination thereof. In some embodiments, the lipophilic mobilizing component may be Brij® 93.

The concentration of the lipophilic mobilizing component that may be present within the mobilizing wax composition may be a minor component of the mobilizing wax composition. In some embodiments, the lipophilic mobilizing component is present in a concentration (v/v %) from about 0.001% to about 10%; 0.001% to about 5%; about 0.001% to about 1.0%; 0.001% to about 0.5%; about 0.001% to about 0.10%; about 0.01% to about 10%; 0.01% to about 5%; about 0.01% to about 1.0%; 0.01% to about 0.5%; about 0.01% to about 0.10%, or any value therebetween. In some embodiments, the lipophilic mobilizing component may be present from about 0.01% to about 0.10%. In some embodiments, the lipophilic mobilizing component may be less than about 1.0%, 0.9%, 0.8%, 0.7%, 0.6%, 0.5%, 0.4%, 0.3%, 0.2%, 0.10%, 0.09%, 0.08%, 0.07%, 0.06%, 0.05%, 0.04%, 0.03%, 0.02% or about 0.01% v/v of the mobilizing wax composition.

Droplet encapsulated by the mobilizing wax composition. The aqueous droplet at least partially encapsulated by the mobilizing wax composition may contain a biological sample of interest, reagent or a micro-object. When the aqueous droplet includes a biological sample, the aqueous droplet may be referred to as a reaction droplet. A reaction droplet may be an aqueous droplet containing a biological sample prior to preparation for an assay, a droplet containing a biological sample undergoing an assay or a droplet containing the product of an assay, which may further be detectable. The reaction droplet may further include reagents for assay preparation, assay reaction or detection and may further contain any of the components from a carrier droplet including but not limited to beads. When a droplet at least partially encapsulated by the mobilizing wax composition contains a micro-object, the micro-object may include one or more of a bead, a biological cell, subcellular portion of a cell or any combination thereof. The bead(s) may be magnetic beads. A subcellular portion of a cell may be or include a nucleus or a ribosome.

In some embodiments, the mobilizing wax composition comprises a liquid wax including liquid paraffin oil and a lipophilic mobilizing component including Brij® 93 (e.g., Polyethylene glycol oleyl ether) at a 0.05% v/v concentration in the mobilizing wax composition.

Uses. The compositions and methods described herein may be used for preventing fouling and evaporation in air-matrix DMF devices and may enable facile and reliable execution of any chemistry protocols on DMF with the requirement for a temperature higher than the ambient temperature. Such protocols include, but are not limited to, DNA/RNA digestion/fragmentation, cDNA synthesis, PCR, RT-PCR, isothermal reactions (LAMP, rolling circle amplification-RCA, Strand Displacement Amplification-SDA, Helicase Dependent Amplification-HDA, Nicking Enzyme Amplification reaction-NEAR, Nucleic acid sequence-based amplification-NASBA, Single primer isothermal amplification-SPIA, cross-priming amplification-CPA, Polymerase Spiral Reaction-PSR, Rolling circle replication-RCR), as well as ligation-based detection and amplification techniques (ligase chain reaction-LCR, ligation combined with reverse transcription polymerase chain reaction-RT PCR, ligation-mediated polymerase chain reaction-LMPCR, polymerase chain reaction/ligation detection reaction-PCR/LDR, ligation-dependent polymerase chain reaction-LD-PCR, oligonucleotide ligation assay-OLA, ligation-during-amplification-LDA, ligation of padlock probes, open circle probes, and other circularizable probes, and iterative gap ligation-IGL, ligase chain reaction-LCR, over a range of temperatures (37-100° C.) and incubation times (≥2 hr). Additional protocols that can be executed using the systems and methods described herein include hybridization procedures such as for hybrid capture and target enrichment applications in library preparation for next generation sequencing (NGS). For these types of applications, hybridization can last up to about 3 days (72 h). Other protocols include end-repair, which can be done, for example, with some or a combination of the following enzymes: DNA Polymerase I, Large (Klenow) Fragment (active at 25° C. for 15 minutes), T4 DNA Polymerase (active at 15° C. for 12 minutes), and T4 Polynucleotide Kinase (active at 37° C. for 30 minutes). Another protocol includes A-Tailing, which can be done with some or a combination of the following enzymes: Taq Polymerase (active at 72° C. for 20 minutes), and Klenow Fragment (3'→5' exo-) (active at 37° C. for 30 minutes). Yet another protocol is ligation by DNA or RNA ligases.

In other applications, the mobilizing waxes described herein may alternatively be employed in bench top experimentation as isolating layers in a variety of sample preparation, amplification and hybridization procedures, including but not limited to ligation, digital PCR, RT-PCR, and any of the protocols mentioned herein.

Manipulation and Processing of Encapsulated Droplets

Although the encapsulation of droplets in wax may prevent or reduce evaporation while executing chemistry protocols at elevated temperatures, after protocol completion, it has been discovered that when the droplet is removed and separated from the wax, e.g., by driving the droplet using the electrodes of the DMF apparatus, a small amount of liquid wax remains with the droplet as a coating even when the aqueous droplet is moved away from the wax, and that this wax coating may prevent or interfere with subsequent processing and analysis of the reaction droplet. Therefore, in some embodiments, the wax encapsulated reaction droplet can be accessed through the wax coating using the systems and methods described herein, which enables facile and reliable execution of downstream biochemical processes.

To access the reaction droplet through the wax coating after the reaction droplet has been separated from the bulk liquid wax in the heating zone, a droplet including an additional hydrophobic (e.g., oil) material may help merge with the wax encapsulated reaction droplet. For example, a carrier droplet (i.e., an aqueous droplet enclosed in a thin layer of oil) can be merged with the encapsulated reaction droplet. The carrier droplet gains access to the reaction droplet by having the oil from the carrier droplet dissolve and/or merge with the thin wax layer encapsulating the reaction droplet. Other materials other than oil may be used by the carrier droplet to break through the wax layer encapsulating the reaction droplet. For example, materials that are immiscible with the aqueous reaction droplet and are capable of dissolving in the wax may be used, such as carbon tetrachloride, chloroform, cyclohexane, 1,2-dichloroethane, dichloromethane, diethyl ether, dimethyl formamide, ethyl acetate, heptane, hexane, methyl-tert-butyl ether, pentane, toluene, 2,2,4-trimethylpentane, and other organic solvents. Other materials that may be used to merge the carrier droplet into the wax encapsulated droplet include ionic detergents such as cetyltrimethylammonium bromide, Sodium deoxycholate, n-lauroylsarcosine sodium salt, sodium n-dodecyl Sulfate, sodium taurochenodeoxycholic; and non-ionic detergents such as dimethyldecylphosphine oxide (APO-10), dimethyldodecylphosphine oxide (APO-12), n-Dodecyl-β-D-maltoside (ULTROL®), n-dodecanoylsucrose, ELUGENT™ Detergent, GENAPOL® C-100, HECAMEG®, n-Heptyl β-D-glucopyranoside, n-Hexyl-b-D-glucopyranoside, n-Nonyl-b-D-glucopyranoside, NP-40 Alternative, n-Octanoylsucrose, n-Octyl-b-D-glucopyranoside, n-Octyl-b-D-thioglucopyranoside, PLURONIC® F-127, Saponin, TRITON® X-100, TRITON® X-114, TWEEN® 20, TWEEN® 80, Tetronic 90R4. In some embodiments, a carrier droplet encapsulated with the mobilizing wax composition may also be used to break through the wax encapsulating the reaction droplet. In this manner, other materials may be added to the reaction droplet through merging with the carrier droplet to form a combined droplet, which is itself at least partially encapsulated with mobilizing wax.

For example, FIG. 6 illustrates an apparatus 600 similar or the same as that shown in FIGS. 1A-4C. The apparatus includes a DMF device interfaced to one or more heating elements placed below or within the bottom DMF substrate, hence generating discrete heating zones (not shown) on the bottom DMF substrate, where reactions may be performed with the encapsulated droplets described herein. Alternatively, the heating element can be placed above or within the top substrate to form a heating zone on the top substrate. However, forming the heating zone on the bottom substrate allows visual access. In some embodiments, the top plate or the bottom plate can be part of a removable cartridge that is combined with the other plate and electronics to form the working DMF device. In some embodiments, on the bottom substrate, one or more hydrophilic regions may be printed or otherwise formed or disposed around the actuating electrodes in the electrode array 604, which may be used to contain or control quantities of liquid wax 606 that may be introduced onto the substrate. In some embodiments, liquid wax may be held at this region, which may additionally be a droplet preparation zone 602. In other embodiments, liquid wax may be introduced in a mixture with the reaction droplet, e.g. an aliquot of mixed fluids dispensed, for example, by a pipettor.

As described herein, in some embodiments, a reaction droplet 608 can be transported or introduced directly to the droplet preparation zone 602 containing the mobilizing wax 606 along a path of actuating electrodes, which may be a relatively narrow path formed by a single line of actuating electrodes to the droplet preparation zone 602. Then the reaction droplet 908 is encapsulated by wax 606 as shown in frame i of FIG. 6, thereby preventing or reducing evaporation from the reaction droplet 608 during the reaction protocol. Depending on the materials present within the reaction droplet 608, mobility may be very limited or nonexistent, without the encapsulation by the mobilizing wax 606. The hydrophilic region, if present surrounding the droplet preparation zone 602 functions to pin or localize the liquid mobilizing wax 606 in place within the droplet preparation zone 602 and allows the encapsulated reaction droplet 610 to break away as described below.

As shown in FIG. 6 (frames ii-iv), the process of breaking away or separating the at least partially encapsulated reaction droplet 608 from liquid wax 606 can be accomplished by driving the aqueous reaction droplet 608 away from the droplet preparation zone 602 and excess liquid wax 606 by actuating the actuating electrodes in the droplet preparation zone 602 and path. As the aqueous reaction droplet 608 is actuated away from the droplet preparation zone 602, the hydrophilic region 602 surrounding the liquid wax 606, if present, may help to hold the liquid wax 606 in place as the reaction droplet 608 moves away from the droplet preparation zone 602, which causes the liquid wax 606 encasing the droplet 608 to begin to neck and eventually break off from the droplet 608, thereby leaving trace or small quantities of liquid wax 606 surrounding the separated reaction droplet 608, creating the at least partially encapsulated reaction droplet 610.

Because the reaction droplet may be surrounded by a thin layer of liquid wax 606 after separation from the droplet preparation zone 602, it may be difficult to merge the encapsulated reaction droplet 610 with another aqueous droplet since the liquid wax coating of the at least partially encapsulated reaction droplet 610 may act as a barrier. Therefore, to facilitate merging of an encapsulated reaction droplet 610 with another droplet, a carrier droplet 612 can be used to merge with the encapsulated reaction droplet 610 as shown in frame v of FIG. 6 (frame v). The carrier droplet 612 can be an aqueous droplet that is coated with a thin layer of oil or another organic solvent as described above. The aqueous portion of the carrier droplet 612 can include additional reagents, beads coated (or not) with DNA/RNA probes or antibodies or antigens for performing separations, uncoated beads, magnetic beads, beads coated with a binding moiety, solid phase reversible immobilization (SPRI) beads, water for dilution of the reaction droplet, enzymes or other proteins, nanopores, wash buffers, ethanol or other alcohols, formamide, detergents, and/or other moieties for facilitating further processing of the encapsulated reaction droplet 610.

Figure 7A:
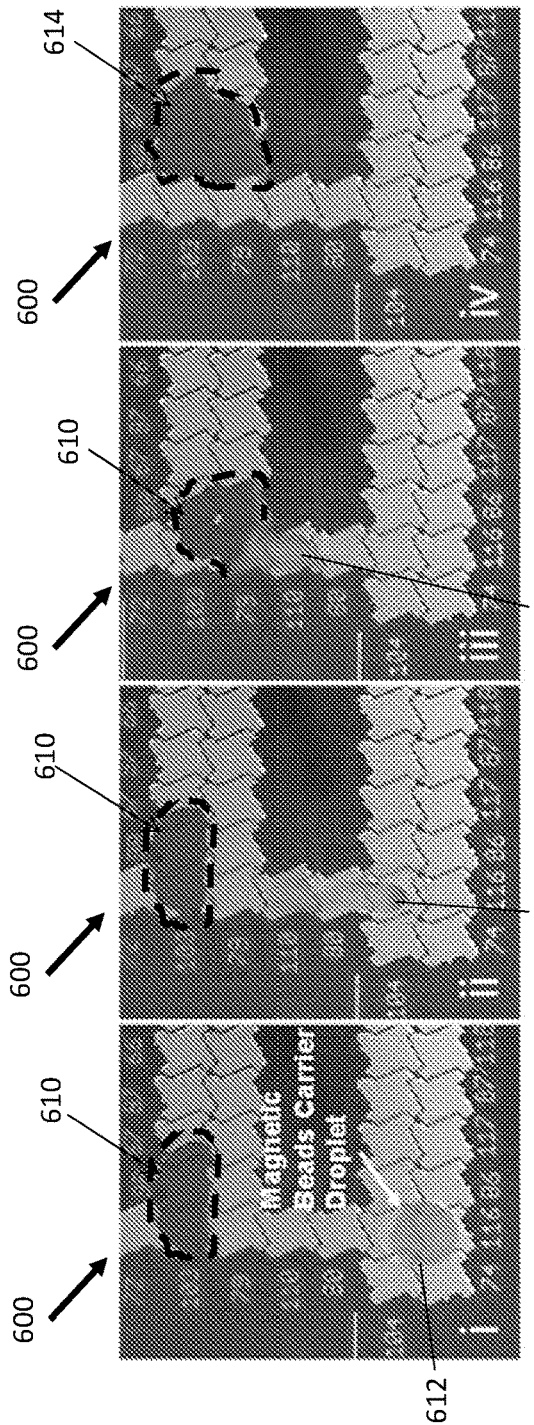
FIGS. 7A-7C are top views of droplet manipulation according to some embodiments of the disclosure.

In one embodiment of merging an encapsulated reaction droplet 610 with a carrier droplet 612 which contains magnetic beads is shown in FIG. 7A (frames i-iv). The carrier droplet 612 and the encapsulated reaction droplet 610 are moved by the actuating electrodes to the same location, the thin layer of oil surrounding the carrier droplet 612 can merge with the thin layer of liquid wax surrounding the encapsulated reaction droplet 610, thereby facilitating the merger of the aqueous portions of the two droplets 610, 612 to form an at least partially encapsulated combined droplet 614.

Figure 7B:
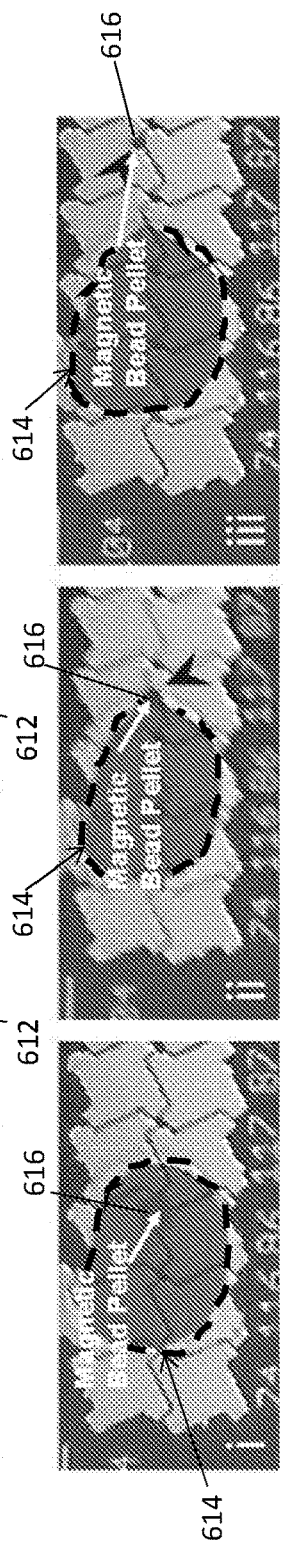
Figure 7C:
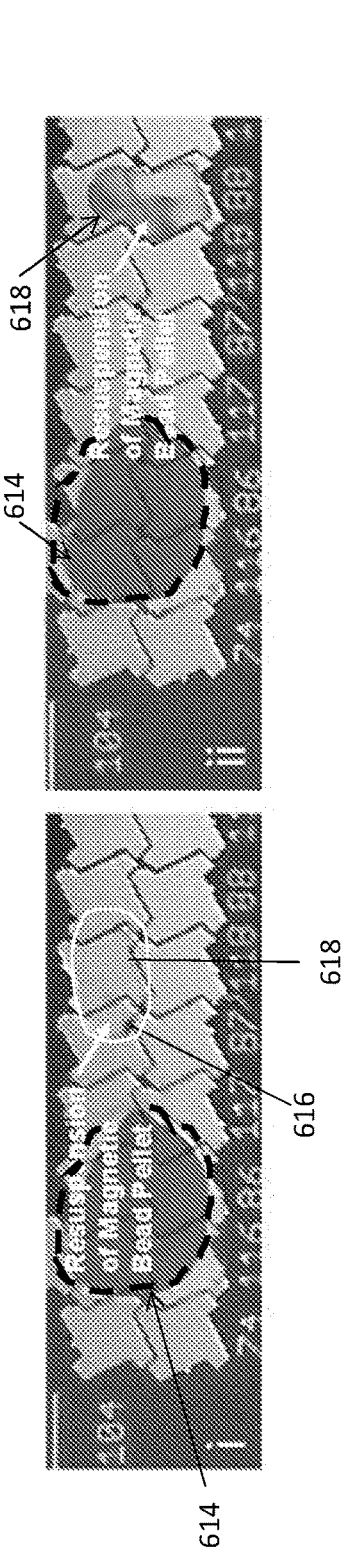

After the carrier droplet 612 has been merged with the encapsulated reaction droplet 61, further processing of the at least partially encapsulated combined droplet 614 can proceed, such as extracting an analyte from the combined droplet 614 and/or perform other steps such as hybridizing capture probes, digesting the reaction product using an enzyme, amplifying the reaction product with a set of primers, and the like. For example, the carrier droplet 612 can be carrying beads for extracting the analyte, e.g., DNA or RNA or proteins. When the droplets are merged, the beads, which can be magnetic, can be used to mix the combined droplet 614 by application of a magnetic field. The target analyte binds to the beads, which can be immobilized against the substrate by the magnetic field to form a bead pellet 616, as shown in FIG. 7B (frame i). Next, the combined droplet 614 can be moved away from the immobilized bead pellet 616, leaving the bead pellet 616 with bound analyte on the substrate, as shown in FIG. 7B (frames ii-iii). The combined droplet 614 can be moved away from the immobilized bead pellet 616 by actuating the electrodes. Alternatively, the combined droplet 614 can be held in place while the bead pellet 616 is moved away from the combined droplet 614. The bead pellet 616 can be moved away and separated from the combined droplet 614 by, for example, moving the magnetic field (e.g., by moving the magnet generating the magnetic field) that is engaging the bead pellet 616 away from the combined droplet 614. In some embodiments, the combined droplet 614 can be actively immobilized through actuation of the electrodes in contact with the droplet and/or surrounding the droplet. Alternatively or in addition, the droplet 614 can be passively immobilized through natural adhesive forces between the droplet and substrate on which the droplet is contacting, as well as physical structures, such as retaining walls that partially surround the combined droplet 614 while having an opening for passing the bead pellet 616. As shown in FIG. 7C (frames i and ii), an aqueous droplet 618 can be moved over the bead pellet 616 to re-suspend the beads with the bound analyte.

EXPERIMENTAL

Apparatus: DMF devices (e.g., FIGS. 1A-4C) were fabricated with 15 mm thick PCB substrates bearing copper (43 μm thick) plated with nickel (185 μm) and gold (3.6 μm) for electrodes and conductive traces. Actuation electrodes (each 10 mm×10 mm) were formed by conventional photolithography and etching, and were coated with soldermask (~15 μm) as the dielectric. The electrical contact pads were masked with polyimide tape (DuPont; Hayward, CA), and the substrate was spin-coated with a 50 nm layer of Teflon-AF (1% wt/wt in Fluorinert FC-40, 1500 rpm for 30 sec) and then baked at 100° C. for 3 h. The top plate of the DMF device, consisting of a glass substrate coated uniformly with un-patterned indium tin oxide (ITO) (Delta Technologies Ltd; Stillwater, MN) with 5.5 mm diameter PDMS plugs was spin-coated with 50 nm of Teflon-AF, as described above.

Experiment 1. Movability Assay. The movability by DMF test was probed to test the motility of a commercially available reagent, SureSelect Fast Hybridization Buffer (Agilent) which is known to foul DMF surfaces. Three conditions were assayed for movability by DMF: 1) fast hybridization buffer droplet (30 μL); 2) fast hybridization buffer droplet (30 μL) enclosed with wax droplet (60 μL); and 3) fast hybridization buffer droplet enclosed with wax droplet (60 μL) infused with Brij® 93 (Polyethylene glycol oleyl ether, 0.05% v/v, Sigma Aldrich Catalog No. 388866). Driving potentials were typically ~300 V and the actuation was automated to keep the driving conditions equivalent for all three sample droplets.

At least three replicates of each experimental condition were evaluated on three separate devices to account for inter-device variation. Movability was defined as the capacity to move droplets across a series of 10 electrodes. As shown in FIG. 1A, all three droplets had a similar starting point and had equivalent paths to travel to the desired endpoint ("Finish Line"). The volume of the aqueous portion of droplets 102, 104, 106 were equivalent across all three samples, and the volume of the encapsulating wax or wax/infused non-ionic surfactant was kept equivalent for the two encapsulated droplets 104, 106. As shown in FIG. 1B, after actuation by DMF, the hybridization buffer only droplet 102 and the hybridization buffer droplet 104 encapsulated with wax (without a lipophilic mobilizing component) were non-mobile. In comparison, the droplet 106 enclosed with wax containing 0.05% lipophilic mobilizing component (e.g., Brij® 93, e.g., Polyethylene glycol oleyl ether) was mobile across 10 electrodes and was the only droplet to be capable of being driven to the desired endpoint. Thus the lipophilic mobilizing component as described herein (and in particular a lipophilic mobilizing component having a hydrophilic-lipophilic balance (HLB) less than 7) permitted the movement despite surface fouling. In all cases shown, none of these droplets (or the lipophilic mobilizing components) included a hydrophilic polymer additive (such as a nonionic surfactant, e.g., TWEEN). In some variations the wax and hydrophilic mobilizing component may include a hydrophilic polymer additive comprises a nonionic surfactant.

Experiment 2. Movability Assay Post Incubations. Incubation at ambient and elevated temperatures is known to be capable of inducing fouling and reagents required for pre-sequencing sample prep, including adapter ligations and PCR amplifications, can also induce surface fouling.

Movability by DMF after incubation at different temperature regimes was probed using known fouling solutions: SureSelect fast hybridization buffer (Agilent), and Herculase Fusion DNA polymerase PCR mastermix (Agilent).

Three different reagent-containing droplets were assayed for movability by DMF and 2) post-thermocycle incubation for the Herculase Fusion PCR mastermix (95□ for 2 min; 10 cycles: 95° C. for 30 sec, 58° C. for 30 sec; 72° C. for 60 sec; 72° C. for 5 min) and 3) SureSelect fast hybridization mix (60 cycles: 65° C. for 1 min, 37° C. for 3 sec).

A. Ligation using Isothermal Incubation. Three droplets, each containing the same amount of sample and KAPA Hyper ligation mastermix (13 μL, Kappa Biosystems), at concentrations according to the manufacturer's instructions (e.g., "reaction droplet") were introduced to the DMF 200 surface. The first droplet 202 was not encapsulated. The second droplet 204 was encapsulated in liquid wax, but did not include Brij®93. The third droplet 206 was encapsulated in liquid wax containing lipophilic mobilizing component (e.g., Brij®93, 0.05% v/v). The amount of encapsulating liquid was the same for droplets 204 and 206 (as in Experiment 1). FIG. 2A showed droplets 202, 204, and 206 after introduction to the surface but before any driving voltage was applied. Driving voltage as in Experiment 1 was applied to drive the droplets 202, 204, 206 to an incubation point, along a path of equivalent length. Droplet 202 immediately fouled the DMF surface and became non-mobile. In contrast, droplet 204 containing ligation reagent/wax and droplet 206 containing ligation reagent/wax including Brij® 93 were mobile to reach the incubation zone (process performed at room temperature). FIG. 2B shows the location of the droplets after driving from the start point. Incubation was performed for 30 min at RT. The droplets 202, 204, 206 were all subjected to the driving voltage as above, resulting in movement of only one droplet. As shown in FIG. 2C, droplet 202 remained immobile at its first starting location; droplet 204 containing ligation reagent/encapsulating wax only also became non-mobile and was not able to be moved from the incubation zone. Droplet 206, containing ligation reagent/encapsulating wax with lipophilic mobilizing component was capable of being driven to the pre-selected finish line.

Figures 3A, 3B, 3C:
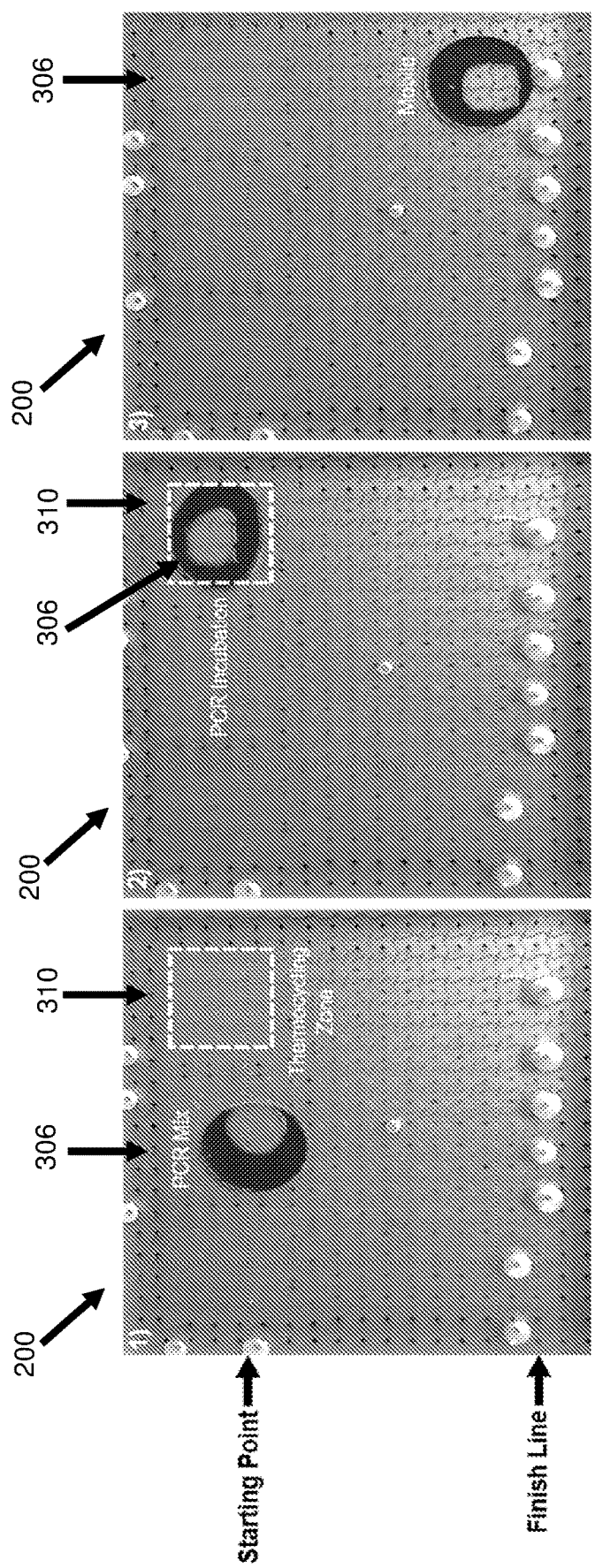
FIGS. 3A-3C are top views of an exemplary droplet upon the surface of an air-matrix DMF apparatus demonstrating portability after exemplary manipulations according to some embodiments of the disclosure.

B. PCR Thermocycling Incubation. Herculase Fusion DNA polymerase PCR mastermix (Agilent) (50 microliters) was encapsulated within 100 microliters of liquid wax incorporating lipophilic mobilizing component (e.g., Brij®93) (0.05% v/v) as above forming droplet 306 upon introduction to an introduction location upon the DMF 200 surface (FIG. 3A). The droplet was successfully driven, under similar voltage conditions as in Experiment 1, to a thermocycling zone 310, as shown in FIG. 3B. Thermocycling, using cycles of 95° C. for 2 min; 10 cycles: 95° C. for 30 sec, 58° C. for 30 sec; 72° C. for 60 sec; 72° C. for 5 min) was performed for an extended period of hours. Droplet 306 was then successfully driven to the preselected finish point upon DMF 200 surface, as shown in FIG. 3C. A droplet including an equivalent volume (50 microliters) of the same PCR mix but encapsulated in 100 microliters of liquid wax, without a lipophilic mobilizing component was not able to be moved to the thermocycle zone (data not shown).

C. Hybridization Incubation. A hybridization reaction using SureSelect fast hybridization buffer (Agilent) was performed within the DMF apparatus 200.

A droplet 406 including hybridization mix (30 μL) surrounded with wax (60 μL) containing lipophilic mobilizing component (e.g., Brij® 93) was introduced to the DMF 200 surface as shown in FIG. 4A. Droplet 406 was successfully driven to the thermocycling zone 410 as shown in FIG. 4B. Thermocycling was performed (60 cycles: 65° C. for 1 min, 37° C. for 3 sec). Droplet 406 was then successfully driven after completion of the reaction to the preselected finish line. A corresponding droplet containing the same volume of hybridization reagent and encapsulating liquid wax that did not contain a lipophilic mobilizing component was not mobile post thermocycles incubation (data not shown).

This anti-fouling strategy is not limited to the specific applications shown in these examples but may be utilized for other reactions requiring incubation of reagents in a static (i.e., not moving) droplet for periods of time, thus permitting reactions to reach completion while still retaining mobility.

Figure 5:
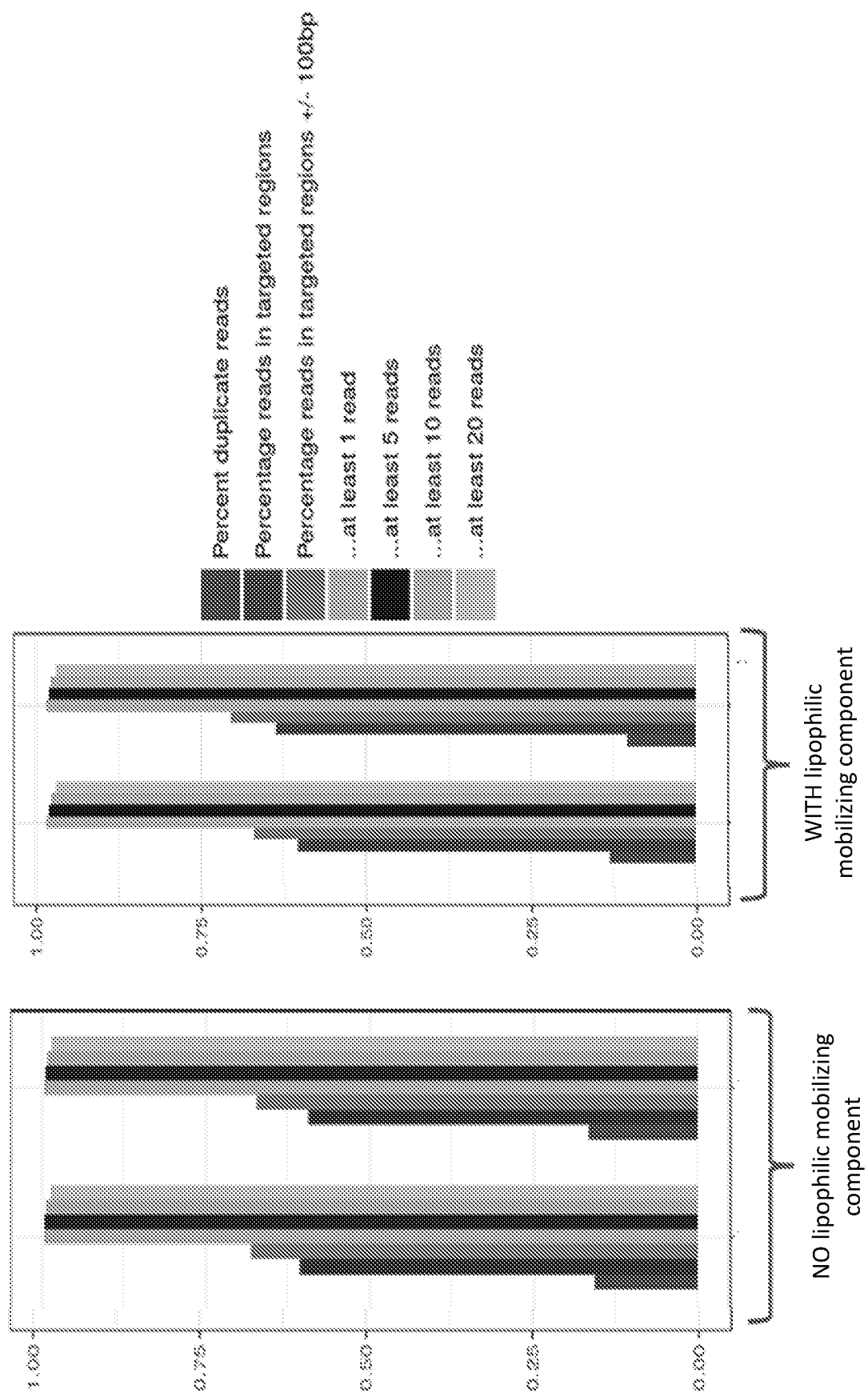
FIG. 5 is a graphical representation of NGS sequencing results for materials recovered from exemplary droplets according to some embodiments of the disclosure.

Experiment 4. Effects of Liquid Wax With Lipophilic Molecules on Assays. To confirm using liquid wax infused with lipophilic mobilizing component (e.g., 0.05% v/v of Brij® 93) did not negatively impact the activity of assays and/or reduce the type or yield of the products observed, we implemented a hybridization-based enrichment reaction (for analyzing specific genetic variants in samples) with and without a lipophilic mobilizing component in wax to the hybridization solution. As shown in FIG. 5, the presence of lipophilic mobilizing component (e.g., Brij®93) in liquid wax does not adversely affect hybridization efficiency, as indicated by examination of standard sequencing metrics (% duplicate reads; % on target; % on target +/−100 bp; and coverage at 1×, 5×, 10× and 20×) the sequencing data of libraries are essentially identical to that observed without lipophilic mobilizing component.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

In general, the term "micro-object" refers to any microscopic object that may be incorporated within the droplets described herein. Non-limiting examples of micro-objects include: inanimate micro-objects such as microparticles; micro-beads (e.g., polystyrene beads, Luminex™ beads, or the like); magnetic beads, microrods; microwires; quantum dots and the like; biological micro-objects such as cells (e.g., embryos, oocytes, ova, sperm cells, cells dissociated from a tissue, eukaryotic cells, protist cells, animal cells, mammalian cells, human cells, immunological cells, hybridomas, cultured cells, cells from a cell line, cancer cells, infected cells, transfected and/or transformed cells, reporter cells, prokaryotic cells, and the like); biological organelles; vesicles, or complexes; synthetic vesicles; liposomes (e.g., synthetic or derived from membrane preparations); or a combination of inanimate micro-objects and biological micro-objects (e.g., microbeads attached to cells, liposome-coated micro-beads, liposome-coated magnetic beads, or the like). Beads may further have other moieties/molecules covalently or non-covalently attached, such as fluorescent labels, proteins, small molecule signaling moieties, antigens, or chemical/biological species capable of use in an assay.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of preventing surface fouling within an air-matrix digital microfluidic (DMF) apparatus, the method comprising:
    introducing an aqueous droplet into an air gap of the air-matrix DMF apparatus which is formed between a first plate and a second plate of the air-matrix DMF apparatus; and
    encapsulating the aqueous droplet within a sheath of a mobilizing wax composition comprising a liquid wax component and a lipophilic mobilizing component, wherein the liquid wax component comprises a tetradecane or hexadecane and is a liquid at temperatures from 4° C. to 100° C., and the lipophilic mobilizing component comprises a non-ionic surfactant having a hydrophilic-lipophilic balance (HLB) less than 7, wherein the lipophilic mobilizing component comprises Polyethylene glycol oleyl ether, and is mixed with the wax component in a concentration (v/v %) from 0.01% to about 0.1%, wherein the lipophilic mobilizing component forms a layer at a surface of the water-liquid wax interface so that a hydrophilic head group of the lipophilic polymer is oriented towards water and a hydrophobic tail of the lipophilic polymer is oriented toward the liquid wax thereby preventing surface fouling by absorption of proteins within the aqueous droplet.

2. The method of claim 1, wherein introducing the aqueous droplet into an air gap comprises combining multiple droplets to form the aqueous droplet within the air gap.

3. The method of claim 1, wherein the mobilizing wax composition is introduced in a mixture with the aqueous drop while introducing the aqueous drop into the air-gap.

4. The method of claim 1, wherein encapsulating the aqueous droplet with the mobilizing wax further comprises transporting, by electrowetting, the aqueous droplet to a droplet preparation zone of the air gap, wherein the droplet preparation zone comprises the mobilizing wax composition.

5. The method of claim 4, wherein moving, by electrowetting, the at least partially encapsulated first aqueous droplet comprises transferring the at least partially encapsulated first aqueous droplet away from the droplet preparation zone so that at least some of the mobilizing wax composition is left behind.

6. The method of claim 1, further comprising merging the encapsulated aqueous droplet with a carrier droplet comprising a second aqueous droplet coated with an oil or an organic solvent in the air gap to form an encapsulated combined aqueous droplet.

7. The method of claim 1, wherein the first plate comprises a plurality of adjacent actuation electrodes, and wherein combining the aqueous droplet with the mobilizing wax comprises applying energy to a subset of the actuation electrodes of the plurality of adjacent actuation electrodes thereby moving the aqueous droplet into contact with the mobilizing wax composition.

8. The method of claim 1, wherein the aqueous droplet comprises a reagent, a micro-object or a combination thereof.

9. The method of claim 1, wherein the aqueous droplet comprises a bead, a biological cell, a subcellular portion of a cell, or any combination thereof.

10. The method of claim 1, wherein the aqueous droplet does not include a hydrophilic polymer additive.

11. The method of claim 1, further comprising:
    moving the encapsulated aqueous droplet, by electrowetting, to a thermal zone of the air gap; and
    regulating the temperature of the encapsulated aqueous droplet to allow a reaction to proceed within the aqueous droplet before transporting the aqueous droplet out of the thermal zone within the air gap.

12. A method of preventing surface fouling within an air-matrix digital microfluidic (DMF) apparatus, the method comprising:
    encapsulating an aqueous droplet within a sheath of a mobilizing wax composition comprising a liquid wax component and a lipophilic mobilizing component, wherein the wax component comprises a tetradecane or hexadecane that is a liquid wax at temperatures from 4° C. to 100° C., and the lipophilic mobilizing component comprises a non-ionic surfactant having a hydrophilic-lipophilic balance (HLB) less than 7, wherein the lipophilic mobilizing component comprises Polyethylene glycol oleyl ether, and is mixed with the wax component in a concentration (v/v %) from 0.01% to about 0.1%, wherein the lipophilic mobilizing component forms a layer at a surface of the water-liquid wax interface so that a hydrophilic head group of the lipophilic polymer is oriented towards water and a hydrophobic tail of the lipophilic polymer is oriented toward the liquid wax thereby preventing surface fouling by absorption of proteins within the aqueous droplet; and
    introducing the encapsulated aqueous droplet into an air gap of the air-matrix DMF apparatus which is formed between a first plate and a second plate of the air-matrix DMF apparatus.

13. A mobilizing wax composition for preventing surface fouling and evaporation during a digital microfluidics (DMF) operation, the mobilizing wax composition comprising:
    a wax component comprising a tetradecane or hexadecane for encapsulating an aqueous droplet, wherein the wax component is a liquid wax at temperatures from 4° C. to 100° C.; and a lipophilic mobilizing component comprising Polyethylene glycol oleyl ether for preventing surface fouling, comprising a non-ionic surfactant having a hydrophilic-lipophilic balance (HLB) less than 7, wherein the lipophilic mobilizing component is mixed with the wax component in a concentration (v/v %) from 0.01% to about 0.1%.

* * * * *